US005667809A

United States Patent [19]
Trevino et al.

[11] Patent Number: 5,667,809
[45] Date of Patent: Sep. 16, 1997

[54] CONTINUOUS FLUOROCHEMICAL MICRODISPERSIONS FOR THE DELIVERY OF LIPOPHILIC PHARMACEUTICAL AGENTS

[75] Inventors: Leo A. Trevino, San Diego; Luis A. Dellamary, San Marcos; Thomas E. Tarara; Jeffry G. Weers, both of San Diego; Helen M. Ranney, La Jolla, all of Calif.

[73] Assignee: Alliance Pharmaceutical Corp., San Diego, Calif.

[21] Appl. No.: 482,176

[22] Filed: Jun. 7, 1995

[51] Int. Cl.⁶ .............................. A61K 9/50; A61K 9/48; A61F 2/02; A61F 6/06
[52] U.S. Cl. .................. 424/501; 424/423; 424/427; 424/430; 424/435; 424/436; 424/443; 424/451; 424/464; 514/937
[58] Field of Search .................... 424/501, 423, 424/427, 430, 443, 435, 436, 451, 464; 514/937

[56] References Cited

U.S. PATENT DOCUMENTS

| | | |
|---|---|---|
| 3,975,512 | 8/1976 | Long, Jr. . |
| 4,814,161 | 3/1989 | Jinks et al. . |
| 5,114,703 | 5/1992 | Wolf et al. . |
| 5,230,884 | 7/1993 | Evans et al. . |
| 5,292,499 | 3/1994 | Evans et al. . |

FOREIGN PATENT DOCUMENTS

| | | |
|---|---|---|
| 0255443 | 2/1988 | European Pat. Off. . |
| 0307087 | 3/1989 | European Pat. Off. . |
| 0311473 | 4/1989 | European Pat. Off. . |
| 0550615 | 8/1995 | European Pat. Off. . |
| 9015807 | 12/1990 | WIPO . |
| 9104664 | 4/1991 | WIPO . |
| 9202560 | 2/1992 | WIPO . |
| 9218165 | 10/1992 | WIPO . |
| 9301798 | 2/1993 | WIPO . |
| 9414415 | 7/1994 | WIPO . |
| 9416742 | 8/1994 | WIPO . |
| 9533447 | 12/1995 | WIPO . |

OTHER PUBLICATIONS

Arbuck, et al. "Clinical Development of Taxol" *J. of National Cancer Institute Monographs* 15: 11–24 (1993).

Blair, et al. "Vitreoperfusion" *Arch Opthalmol* 107: 417–423 (1989).

Hageluken, et al. "Lipophilic β–Adrenoceptor and Local Anesthetics Are Effective Direct Activators of G–Proteins" *Biochemical Pharmacology* 47(10):1789–1795 (1994).

Hughes, et al. "Effect of Acylation on the Ocular Disposition of Acyclovir II: Corneal Permeability and Anti–HSV 1 Activity of 2'–Esters in Rabbit Epithelial Keratitis" *J. Ocular Pharmacology* 9(4):299–309 (1993).

Lewis, et al. "The Use of Perfluorocarbon Liquids in the Repositioning of Posteriorly Dislocated Intraocular Lenses": Opthalmology 100(7): 1055–1059 (1993).

Riess, Jean G. "Fluorocarbon–Based In Vivo Oxygen Transport and Delivery System" *Vox Sanguinis* 61: 225–239 (1991).

Shaffer, et al. "Perfluorochemical Liquid As A Respiratory Medium" *Art. Cells, Blood Subs., and Immob. Biotech.* 22(2):315–326 (1994).

Shaffer, et al. "Liquid Ventilation" *Pediatric Pulmonary* 14: 102–109 (1992).

Tang–Liu, et al. "Lenticular Uptake and Distribution of Xenobiotics and Amino Acids" *J. of Ocular Pharmacology* 8(3):267–277 (1992).

Wolfson, et al. "Pulmonary Administration of Drugs (PAD): A New Approach for Drug Delivery Using Liquid Ventilation" *FASEB* 4: A1105 (1990).

Yokogawa, et al. "Relationships in the Structure–Tissue Distribution of Basic Drugs in the Rabbit" *Pharmaceutical Res.* 7(7):691–696 (1990).

Naito, et al. "Supplement to Perfluorochemical Blood Substitutes" *Technical Information Series No. 5*: 1–177 (1978).

Naito, et al. "Supplement to Perfluorochemical Blood Substitutes" *Technical Information Series No. 7*: 1–119 (1981).

Rowinsky, et al. "Paclitaxel (TAXOL)" *New England Journal of Medicine*: 332(15): 1004–1014 (1995).

Evans, et al. "Formulation and in Vitro Evaluation of Presurized Inhalation Aerosols Containing Isotropic Systems of Lecithin and Water" *Pharmaceutical Res.* 8(5):629–635 (1991).

Banker, et al. *Modern Pharmaceutics*, ed. Marcel Dekker, Inc., New York pp. 31–49 (1991).

Balasubramanian, et al. "Taxol–Lipid Interactions: Taxol–Dependent Effects on the Physical Properties of Model Membrane" *Biochemistry* 33: 8941–8947 (1994).

Prescott, L.F. "The Need for Improved Drug Delivery in Clinical Practice" *Novel Drug Delivery and Its Therapeutic Application* Chapter 1 pp. 1–7, eds. Prescott, et al. (1988).

Riess, Jean. "Hemocompatible Fluorocarbon Emulsions" *Blood Compatible Materials and Devices—Perspectives Towards the 21st Century* Chapter 14 pp. 237–270, eds. Sharma, et al. (1991).

*Primary Examiner*—Carlos A. Azpuru
*Attorney, Agent, or Firm*—Knobbe, Martens, Olson & Bear

[57] ABSTRACT

A method for preparing a pharmaceutical microdispersion exhibiting enhanced bioavailability, including the steps of providing a thermodynamically stable pharmaceutical composition comprising at least one lipophilic pharmaceutical agent incorporated in a physiologically acceptable liquid carrier, the liquid carrier comprising one or more lipophilic solvents such as fluorochemicals and preferably at least one nonfluorinated co-solvent, and combining the stable pharmaceutical composition with an amount of at least one miscible diluent sufficient to initiate phase separation of the lipophilic pharmaceutical agent from the pharmaceutical composition wherein a microdispersion of the pharmaceutical composition is formed. Also disclosed are microdisperse pharmaceutical compositions and kits for forming such compositions.

63 Claims, No Drawings

CONTINUOUS FLUOROCHEMICAL MICRODISPERSIONS FOR THE DELIVERY OF LIPOPHILIC PHARMACEUTICAL AGENTS

FIELD OF THE INVENTION

The present invention generally relates to formulations and methods for the administration of lipophilic pharmaceutical agents to a physiological target site. More particularly, the invention is directed to improved fluorochemical microdispersions that may be used to increase the bioavailability and efficacy of lipophilic compounds having limited solubility in an aqueous physiologic environment. These microdispersions may be formulated so as to facilitate administration, provide extended delivery profiles and increase drug stability, making them particularly suitable for the sustained and controlled delivery of lipophilic pharmaceutical agents.

BACKGROUND OF THE INVENTION

The efficacy of many pharmaceutical agents is predicated on their ability to proceed to the selected target sites and remain there in effective concentrations for sufficient periods of time to accomplish the desired therapeutic or diagnostic purpose. Difficulty in achieving efficacy may be exacerbated by the location and environment of the target site as well as by the inherent physical characteristics of the compound administered. For example, drug delivery via routes that are subject to repeated drainage or flushing as part of the body's natural physiological functions offer significant impediments to the effective administration of pharmaceutical agents. In this respect, delivery and retention problems are often encountered when administering compounds through the respiratory or gastrointestinal tracts. Repeated administration of fairly large doses are often required to compensate for the amount of drug washed away and to maintain an effective dosing regimen when employing such routes. Moreover, the molecular properties of the pharmaceutical compound may impair the absorption through a given delivery route, thereby resulting in a substantial reduction in efficacy. This is particularly true of lipophilic compounds that are not soluble in aqueous environments. For instance, insoluble particulates are known to be subject to phagocytosis and pinocytosis, resulting in the accelerated removal of the compound from the target site. Such reductions in delivery and retention time complicate dosing regimes, waste pharmaceutical resources and generally reduce the overall efficacy of the administered drug.

Unlike many hydrophilic compounds, the delivery of lipophilic drugs by conventional means has been and continues to be problematic. Unfortunately, a number of the most promising therapeutic and diagnostic agents currently under development are bulky polycyclic molecules that tend to be relatively insoluble in water. The substantial physical size of these compounds, coupled with the intrinsic lipophilicity of their molecular structure, has severely limited their use in practical pharmaceutical applications. For instance, the oral administration of lipophilic agents using conventional tablets and capsules suffers the disadvantage of a variable rate of absorption of the administered drug and depends on factors such as the presence or absence of food, the pH of gastrointestinal fluids and gastric emptying rates. Moreover, the insolubility of large lipophilic particulates tends to reduce delivery rates as little drug dissolves in the gastrointestinal liquid and crosses the epithelial barrier before it is excreted. Finally, the degradation of labile drugs by gastric fluids and drug metabolizing enzymes may reduce the drug bioavailability to the point of therapeutic failure (Prescott, L. F., in Novel Drug Delivery and its Therapeutic Application, John Wiley & Sons, New York, 1989, pp. 3–4).

Other delivery routes fare little better when lipophilic compounds are administered using conventional delivery vehicles. The parenteral administration of these water insoluble drugs requires that they be formulated in the form of oil in water emulsions or that they be solubilized into a water miscible phase. This suffers drawbacks associated with the formulation of a suitably stable dosage form that can be delivered by this route; such formulations often contain surfactant systems which, by themselves, may cause toxic side effects. For example, the current method used for the intravenous administration of the highly lipophilic cancer drug Taxol involves the use of a polyoxyethylated castor oil vehicle that has been associated with hypersensitivity reactions including dyspnea, bronchospasm, urticaria, and hypotension (Rowinsky, E. K. and Donehower, R. C., New Eng. J. Med., 1995, 332, 1004). In addition, the intravenous administration of drugs such as Taxol, which exhibit high systemic toxicities, severely limits their therapeutic capacity (Balasubramanian, S. V. and Straubinger, R. M., Biochemistry, 1994, 33, 8941). Thus, despite encouraging results with existing delivery other reference systems, the inherently low bioavailability of these lipophilic compounds at the target site due to inefficient or toxic delivery systems substantially reduces their efficacy.

In spite of the difficulties associated with the delivery of lipophilic drugs, the potential advantages in developing methods to do so are great. Extensive work has been done to show that the membrane permeability, bioavailability and efficacy of drugs often increases with increasing lipophilicity (Banker G. S. and Rhodes, C. T. in "Modern Pharmaceutics", Marcel Dekker, Inc., New York, 1979, pp. 31–49; Hughes, P. M. and Mitra, A. K., J. Ocul. Pharmac., 1993, 9, 299; Yokogawa, K., Nakashima, E., Ishizaki, J., Maeda, H., Nagano, T. and Ichimura, F., Pharm. Res. 1990, 7, 691; Hageluken, A., Grunbaum, L., Nurnberg, B., Harhammer, R., Schunack, W. and Seifert, R., Biochem. Pharmac., 1994, 47, 1789). The development of new systems for the delivery of these compounds could, therefore, significantly increase the therapeutic efficacies for the treatment of a wide variety of indications.

In this respect, one class of delivery vehicles that has shown great promise when used for the administration of pharmaceutical agents is fluorochemicals. During recent years, fluorochemicals have found wide ranging application in the medical field as therapeutic and diagnostic agents. The use of fluorochemicals to treat medical conditions is based, to a large extent, on the unique physical and chemical properties of these substances. In particular, the relatively low reactivity of fluorochemicals allows them to be combined with a wide variety of compounds without altering the properties of the incorporated agent. This relative inactivity, when coupled with other beneficial characteristics such as an ability to carry substantial amounts of oxygen, radioopaqueness for certain forms of radiation and low surface energies, have made fluorochemicals invaluable for a number of therapeutic and diagnostic applications.

For example, various fluorochemical emulsions have been used as oxygen carriers during medical procedures. Conventional oil-in-water emulsions, which may be infused directly into the blood stream, consist of a selected fluorochemical dispersed in the form of droplets in a continuous aqueous phase. Because of the high oxygen-carrying capacity of fluorochemicals, such emulsions are particularly useful as blood substitutes to provide oxygen to the vascular system. After administration of the emulsions, the oxygen dissolved in the dispersed fluorochemical phase is released into the blood. Fluosol® (Green Cross Corp., Osaka, Japan), a formally commercially available oil-in-water emulsion containing fluorochemicals, has been used as a gas carrier to oxygenate the myocardium during percutaneous transluminal coronary angioplasty (R. Naito, K. Yokoyama, Technical Information Series No. 5 and 7, 1981). Fluorochemicals have also been used as contrast enhancement media in radiological imaging by Long (U.S. Pat. No. 3,975,512) and in nuclear magnetic resonance imaging (U.S. Pat. No. 5,114,703). Other proposed medical uses include the treatment of cardiovascular and cerebrovascular diseases, coronary angioplasty, organ preservation and cancer therapy; diagnostic ultrasound imaging and veterinary therapy (Riess J. G., Blood Compatible Materials and Devices: Perspective Towards the 21st Century, Technomics Publishing Co., Lancaster, Pa., Ch. 14, 1991; Riess, J. G., Vox. Sang., 61:225, 1991). Conventional direct fluorochemical emulsions have been described in, for example, EP-A-0 255 443, FR-A-2 665 705, FR-A-2 677 360, FR-A-2 694 559, FR-A-2 679 150, PCT/W090/15807, EP-A-311473 and U.S. Pat. No. 3,975,512.

In addition to the aforementioned oil-in-water emulsion system, neat fluorochemicals and emulsions having a continuous fluorochemical phase have also been used in various medical applications. For instance, neat fluorochemicals are being evaluated for use in liquid ventilation applications. Currently one product, LiquiVent™ (Alliance Pharmaceutical Corp., San Diego, Calif.), is undergoing clinical trials for use in Respiratory Distress Syndrome (RDS). Such compositions could also be used in the treatment of premature infants with underdeveloped lungs. Another product, IMAGENT® GI (Alliance Pharmaceutical Corp., San Diego, Calif., an FDA approved diagnostic agent composed of a neat fluorochemical, is particularly useful for imaging the gastrointestinal (GI) tract. Fluorochemical liquids are also finding potential utility in eye surgery applications, such as the repositioning of posteriorly dislocated intraocular lenses and in the treatment of ocular ischemia (Lewis, H. and Sanchez, G., Ophthalmology, 1993, 100, 1055; Blair, N. P., Baker, D. S., Rhode J. P., and Solomon, M., Arch Ophthalmol, 1989, 107, 417).

While such applications are impressive, the ability to use fluorochemicals to reliably deliver effective amounts of pharmaceutical agents, either in conjunction with fluorochemical mediated therapy or in a separate dosing regime, would be of great benefit. The use of fluorochemical drug delivery vehicles would be particularly favorable for lipophilic drugs that are insoluble in aqueous solutions and present special problems in the aqueous physiological environment. For example, efficient pulmonary administration of pharmaceutical compounds, both lipophilic and hydrophilic, would be especially advantageous. Pulmonary administration of drugs constitutes a difficult problem because the introduction of compounds directly into the lungs cannot be effectively achieved by means of an aqueous solution or by fluorochemical emulsions wherein the continuous phase is also aqueous. Yet, as seen from the applications above, fluorochemicals may easily be introduced to the lung. Such direct administration is critical in the treatment of lung disease as poor vascular circulation of diseased portions of the lung reduces the effectiveness of intravenous drug delivery. In addition to treating pulmonary disorders, fluorochemical pharmaceutical formulations administered to the lung could also prove useful in the treatment and/or diagnosis of disorders such as RDS, impaired pulmonary circulation, cystic fibrosis and lung cancer. In addition to the pulmonary route of administration, fluorochemicals could advantageously be used for the administration of compounds via other routes such as topically, orally, intraperitoneally, or intraocularly.

Work in this area has shown that the pulmonary delivery of biological agents through the alveolar surface may be facilitated when accomplished in conjunction with liquid ventilation (Wolfson, M. R. and Shaffer, T. H., The FASEB J., 1990, 4, A1105), that is, using formulations having an oxygen rich fluorochemical continuous phase. The increased efficacy observed in compounds administered in conjunction with liquid ventilation to the impaired lung may be due to several factors, including the high spreading coefficients of some fluorochemicals on the pulmonary surface, an increase in alveolar surface area due to more effective lung inflation and the delivery of oxygen by the fluorochemical. Shaffer, et al., have also shown that pulmonary administration can increase the biological response of some drugs when compared to intravenous administration (Shaffer, T. H., Wolfson, M. R., Greenspan, J. S. and Rubenstein, S. D., Art. Cells, Blood Sub. & Immob. Biotech., 1994, 22, 315).

Similarly, Kirkland (WO 92/18165) has shown that fluorocarbon liquid admixtures of insoluble particles may be used as effective imaging agents for magnetic resonance imaging or radiography. Kirkland produced these fluorocarbon admixtures through the addition of effervescent powdered components formed using conventional manufacturing techniques and found that the gas given off significantly improves the images obtained.

Yet, despite such successes, the administration of pharmaceutical compounds, particularly therapeutics designed for absorption by the body, is not without difficulties. A significant problem associated with conventional fluorochemical mediated drug delivery is that the large majority of drugs (lipophilic and hydrophilic) are insoluble in the fluorochemical phase. This may present a number of issues involving administration of the compound including stability, particle size, dose reliability, dispersion consistency and ultimately bioavailability. For example, the current method of pulmonary administration involves the preparation of a crude dispersion of the fluorochemical insoluble material and delivery by turbulent flow (Shaffer, T. H., Wolfson, M. R. and Clark, L. C., Pediatric Pulmonology, 1992, 14, 102). Yet, using this technique to deliver fluorochemical insoluble drugs (Shaffer et al., Art. Blood Subs. and Cells Immob. Biotech., 22:1994; Pediatr. Pulmonol., 14:102, 1992) resulted in non-homogenous, unreliable and irreproducible drug delivery due to the inefficient dispersion of the powdered agent in the fluorochemical phase. Moreover, while suitable delivery vehicles of comparable efficacy often exist for hydrophilic compounds, the choice for lipophilic agents is much smaller.

Drug suspensions in volatile chlorofluorocarbon propellants of the current art are often heterogeneous systems which usually require redispersion prior to use. Yet, obtaining a relatively homogeneous distribution of the pharmaceutical compound is not always easy in an "oily" fluorochemical. In addition, these formulations suffer from the disadvantage that they are prone to aggregation of the particles which, in the case of aerosol delivery, can result in clogging of the propellant system and inadequate delivery of the drug. Crystal growth of the suspensions via Ostwald ripening may also lead to particle size heterogeneity and can significantly reduce the shelf-life of the formulation. Another major problem with conventional dispersions, whether they are emulsions or suspensions, is particle coarsening. Coarsening may occur via several mechanisms such as flocculation, fusion, molecular diffusion, and coalescence. Over a relatively short period of time these processes can coarsen the formulation to the point where it is no longer usable. Comparable problems may occur in fluorochemical suspensions designed for other routes of administration such as through the gastrointestinal tract or ocular environment.

A further constraint on such conventional dispersions concerns the distribution of particle sizes. For oral administration, smaller drug particles or crystals, often on the order of 10 nm to 100 nm with large surface areas, are preferred due to their rapid diffusion for the delivery vehicle to the site of action. Unfortunately, it is generally not practical to produce particles having the optimal characteristics using conventional means such as airstreaming or grinding. Accordingly, many current formulations incorporate drug particulates having average particle diameters on the order of a few microns or more.

Several attempts have been made to solve these problems and provide efficient fluorochemical delivery vehicles. For instance, Evans et al. (Pharm. Res., 1991, 8,629; U.S. Pat. 5,292,499; U.S. Pat. 5,230,884) and Jinks et al. (U.S. Pat. 4,814,161) disclose the use of volatile propellants stabilized by lipids for pulmonary drug delivery. Nonetheless, neither teach the use of nonvolatile fluorochemical liquid continuous media for use in these aerosol formulations, and they state that the inclusion of large proportions of high boiling components in these formulations is undesirable. Moreover, Evans et al. limit their disclosure to the solubilization of hydrophilic pharmaceutical compounds with no mention of incorporating hydrophobic compounds.

Accordingly, it is an object of the present invention to provide high bioavailability fluorochemical microdispersions incorporating therapeutic or diagnostic compounds which exhibit improved shelf-lives and stability.

It is a further objective of the present invention to provide pharmaceutical compositions capable of effectively delivering lipophilic pharmaceutical agents.

It is yet a further objective of the present invention to provide a method for the formation of lipophilic pharmaceutical microdispersions exhibiting enhanced bioavailability.

SUMMARY OF THE INVENTION

Generally stated, the present invention accomplishes the aforementioned objectives by providing novel fluorochemical microdispersions which may be used to deliver lipophilic pharmaceutical agents to selected physiological target sites. More specifically, the present invention provides high bioavailability pharmaceutical microdispersions having a liquid fluorochemical continuous phase and a pharmaceutical agent-containing discontinuous phase. In sharp contrast to prior art formulations, the preferred exemplary embodiments of the present invention readily incorporate water insoluble, lipophilic pharmaceutical medicaments and diagnostic compounds for administration as a microdispersion. This advantageously provides an increased bioavailability of the lipophilic agent at the delivery site, leading to more efficacious delivery. The pharmaceutical microdispersions disclosed herein may either be in the form of a suspension or in the form of an emulsion and may be tailored to facilitate the effective delivery of pharmaceutical agents having different degrees of lipophilicity. In addition, the pharmaceutical microdispersions of the present invention may be formulated to resist coarsening and other degradative forces, thereby providing enhanced stability and an extended shelf-life.

It must be emphasized that, unlike prior art suspensions of pharmaceutical compounds in fluorochemicals, the novel microdispersions of the present invention are formed by an induced phase separation. More particularly, in one aspect of the invention the selected lipophilic pharmaceutical agent or agents are first incorporated into a thermodynamically stable composition comprising at least one lipophilic material, such as a fluorochemical, and optionally at least one co-solvent. This composition may be a molecular solution. In preferred embodiments the co-solvent is a short chain alcohol or an alkyl sulfoxide. This composition is then combined with a diluent comprising at least one material soluble in the lipophilic liquid, preferably a fluorochemical. Significantly, the lipophilicity of the diluent is less than the lipophilicity of the thermodynamically stable composition. Accordingly, when combined in sufficient quantity, the diluent initiates a phase separation forcing the lipophilic pharmaceutical agent into a discontinuous phase and forming a pharmaceutical microdispersion having enhanced bioavailability.

As indicated above, the pharmaceutical microdispersions of the present invention may be formed as either an emulsion or as a suspension depending on the individual requirements of the intended dosing regime and administration technique. The final form of the microdispersion may be selected by varying the concentration of the nonfluorinated co-solvent in the thermodynamically stable pharmaceutical composition prior to combining it with the fluorochemical diluent. More specifically, if the final concentration of the co-solvent does not exceed its solubility limit in the combined formulation, it will remain in the fluorochemical continuous phase while the lipophilic pharmaceutical agent undergoes a phase separation to form a discontinuous suspension. Conversely, if the concentration of the nonfluorinated co-solvent exceeds its solubility limit in the combined formulation, the excess amount will be forced out of the fluorochemical continuous phase. In this case, the nonfluorinated co-solvent will associate with the lipophilic pharmaceutical agent to produce a liquid discontinuous phase resulting in an emulsion.

Another aspect of the present invention relates to enhanced bioavailability pharmaceutical formulations produced according to the method described above. In a preferred embodiment these formulations comprise a substantially homogeneous microdispersion of a pharmaceutically effective amount of at least one lipophilic pharmaceutical agent in a liquid continuous phase comprising one or more physiologically acceptable lipophilic fluorochemicals, at least one co-solvent and at least one diluent. As explained previously, the dispersions may be formed as suspensions or reverse emulsions. In either formulation the discontinuous phase will preferably comprise microparticulates having average diameters on the order of 3 μm or less, and more preferably having average diameters significantly less than 1 μm. The colloidal nature of the substantially homogeneous dispersions of the present invention provide enhanced bioavailability due to their rapid dissolution at the target site. Moreover, as the microdispersions of the present invention are produced by a precipitation rather than by mechanical comminution, the homogeneity of the formulation is significantly better than conventional compositions.

The microdispersions of the present invention may also comprise one or more additives which are present in the discontinuous pharmaceutical phase, in the fluorochemical continuous phase, in both of these phases, or at the interface between the phases. The additives may include, for example, mineral salts, buffers, oncotic and osmotic agents, flavoring or palatability agents, nutritive agents, or any other ingredients capable of augmenting the favorable characteristics of the microdispersions including their stability, therapeutic efficacy and tolerance. In particular, the microdispersions may incorporate fluorinated or nonfluorinated surfactants in order to provide additional stability to the formulation and to retard degradation brought about by coarsening.

Yet another aspect of the present invention relates to a method for delivering one or more lipophilic pharmaceutical agents to a physiologic target site. This method comprises the steps of providing a pharmaceutical formulation comprising a substantially homogeneous microdispersion of at least one lipophilic pharmaceutical agent in a liquid continuous phase where the liquid continuous phase comprises one or more lipophilic fluorochemicals, at least one nonfluorinated co-solvent and at least one fluorochemical diluent; and introducing a pharmaceutically effective amount of the pharmaceutical formulation to a physiologic site. It should be emphasized that, in preferred embodiments, the formulations may be administered using a number of different routes including, but not limited to, the gastrointestinal tract, the respiratory tract, topically, intramuscularly, intraperitoneally, nasally, pulmonarily, vaginally, rectally, aurally, orally or intraocularly. Similarly, any lipophilic pharmaceutical agent that may be incorporated into the thermodynamically stable composition may be effectively administered using the method outlined above. Preferably, the pharmaceutical agents will have a log of the octanol/water partition coefficient of at least 0.5, and more preferably of at least 2 while comprising less than 20% w/v of the formulation.

Thus, one aspect of the present invention is a method for preparing a pharmaceutical microdispersion exhibiting enhanced bioavailability, the method comprising the steps of: providing a thermodynamically stable pharmaceutical composition comprising at least one lipophilic pharmaceutical agent incorporated in a physiologically acceptable liquid carrier, the liquid carrier comprising one or more lipophilic fluorochemicals and at least one nonfluorinated co-solvent; and combining the stable pharmaceutical composition with an amount of at least one fluorochemical diluent sufficient to initiate phase separation of the at least one lipophilic pharmaceutical agent from the pharmaceutical composition wherein a pharmaceutical microdispersion is formed. The microdispersion is a suspension when the co-solvent is not part of the discontinuous phase; otherwise, the microdispersion is an emulsion. Preferred lipophilic perfluorchemicals are halogenated fluorochemicals, fluorocarbon-hydrocarbon diblock or triblock compounds, halogenated ethers, polyethers, fluorocarbon-hydrocarbon esters, fluorocarbon-hydrocarbon thioesters, fluorocarbon-hydrocarbon amines and fluorocarbon-hydrocarbon amides. By another definition, preferred lipophilic fluorochemicals are $C_nF_{2n+1}X$, $XC_nF_{2n}X$, where n=3–8, X=Br, Cl or I; $C_nF_{2n}+1-C_mH_{2m+1}$, $C_nF_{2n+1}CH=CHC_mH_{2m+1}$, where n=2–8 m=2–6; $C_pH_{2p+1}-C_nF_{2n}-C_mH_{2m+1}$, where p=2–6, m=2–6 and n=2–8; $XC_nF_{2n}OC_mF_{2m}X$, $XCF_2OC_nF_{2n}OCF_2X$, where n=1–4, m=1–4, X=Br, Cl or I; $C_nF_{2n}-O-C_mH_{2m+1}$, where n=2–8; m=2–6; $C_pH_{2p+1}-O-C_nF_{2n}-O-C_mH_{2m+1}$, where p=2–6, m=2–6 and n=2–8; 1-bromo-F-octane (n-$C_8F_{17}$Br); 1-bromo-F-heptane (n-$C_7F_{15}$Br); 1-bromo-F-hexane (n-$C_6F_{13}$Br); perfluorooctyl chloride (n-$C_7F_{15}$Cl); 1, 6-dichloro-F-hexane (n-$ClC_6F_{12}$Cl); 1, 4-dichloro-F-butane (n-$ClC_4F_8$Cl); 1, 4-dibromo-F-butane and 1,6-dibromo-F-hexane. In one embodiment of the method, the lipophilic pharmaceutical agent is selected from the group consisting of respiratory drugs, antibiotics, anti-inflammatories, antineoplastics, anesthetics, ophthalmic agents, chemotherapeutic agents, cardiovascular agents, imaging agents and combinations thereof. Preferably, the lipophilic pharmaceutical agent exhibits a log of the octanol/water partition coefficient (Log Po/w) greater than about 0.5.

The fluorochemical diluent is preferably selected from the group consisting of bis(F-alkyl) ethenes, cyclic fluorocarbons, perfluorinated amines, brominated perfluorocarbons, iodinated perfluorocarbons, chlorinated perfluorocarbons, perfluorooctyl chloride, perfluorooctyl hydride, perfluoroalkylated ethers perfluoroalkylated polyethers, fluorocarbon-hydrocarbon compounds and combinations thereof. The diluent is less lipophilic than the lipophilic fluorochemical. The co-solvent is advantageously selected from ethers, alcohols, alkyl sulfoxides other non-fluorinated biocompatible solvents, and combinations thereof.

The method may also include the step of introducing a therapeutically beneficial amount of a physiologically acceptable gas into the pharmaceutical microdispersion. Further, a fluorinated or nonfluorinated surfactant may be used in the composition. In a preferred embodiment, the lipophilic pharmaceutical agent is less than approximately 20% w/v and the concentration of the lipophilic fluorochemical is less than approximately 50% v/v. The microdispersion may advantageously have an average particle diameter less than approximately 3 µm, more preferably less than approximately 1 µm.

The present invention also includes a pharmaceutical microdispersion exhibiting enhanced bioavailability prepared according to the foregoing method. It also includes a high bioavailability pharmaceutical formulation comprising a substantially homogeneous microdispersion of a pharmaceutically effective amount of at least one lipophilic pharmaceutical agent in a liquid continuous phase, the liquid continuous phase comprising one or more physiologically acceptable lipophilic fluorochemicals, at least one co-solvent and at least one fluorochemical diluent. As above, the microdispersion may be a suspension or an emulsion. The various materials in the formulation may be as described above in connection with the method. In one embodiment, the concentration of the lipophilic pharmaceutical agent is less than approximately 20% w/v and the concentration of the one or more lipophilic fluorochemicals is less than approximately 50% v/v. Preferably, the microdispersion has an average particle diameter of less than about 3 or 1 µm, and may be in the nanometer range; e.g., 1, 2, 3, 4, 5, 7, 8, or 10 nm.

In one embodiment, a therapeutically beneficial amount of a physiologically acceptable gas is incorporated in the liquid continuous phase. In another, the formulation includes a fluorinated or nonfluorinated surfactant.

The invention further includes a method for delivering one or more lipophilic pharmaceutical agents to a physiologic target site, the method comprising the steps of: providing a high bioavailability pharmaceutical formulation comprising a substantially homogeneous microdispersion of at least one lipophilic pharmaceutical agent in a liquid continuous phase, the liquid continuous phase comprising one or more lipophilic fluorochemicals, at least one nonfluorinated co-solvent and at least one fluorochemical diluent; and introducing a pharmaceutically effective amount of the high bioavailability pharmaceutical formulation to a physiologic target site. The various components of the formulation may be as described above. The introduction of the pharmaceutical formulation to the physiological target site may advantageously be accomplished topically, subcutaneously, intramuscularly, intraperitoneally, nasally, pulmonarily, vaginally, rectally, aurally, orally or ocularly.

In yet another embodiment of the present invention, there is provided a method for preparing a pharmaceutical material, comprising the steps of: providing a first composition of a lipophilic first liquid combined with a pharmaceutical agent in a single continuous phase, and adding to the first composition a sufficient amount of a second liquid less lipophilic than the first liquid that is miscible in the first liquid to cause phase separation of the pharmaceutical agent to form a microdisperse discontinuous phase. The discontinuous phase can be either an emulsion or a suspension. Preferably, the first liquid and/or the second liquid is a fluorocarbon. Optionally, the composition includes a co-solvent to facilitate combination of the pharmaceutical agent with the first liquid, although such is not required. The co-solvent is preferably a nonfluorocarbon. The discontinuous phase can comprise the co-solvent and the pharmaceutical agent, or it can comprise just the pharmaceutical agent. In one embodiment of the method, the first composition is stored for 6, 12, or 18 hours before combining it with the second liquid. In another, it is stored for 2, 3, or 5 days, or 1, 2, 4, 10, or 20 weeks, or 6 months, 12 months, 18 months, 24 months up to an indefinite amount of time before use prior to the adding step.

Finally, the present invention includes a kit for preparing a pharmaceutical preparation, comprising: a first container having therein a first composition comprising a first lipophilic liquid fluorocarbon and a pharmaceutical agent in a single continuous phase; and a second container having therein a second liquid miscible with the first liquid, wherein the second liquid is less lipophilic than the first liquid, such that upon combination of the first composition and the second liquid, a phase separation of the pharmaceutical agent occurs to form a microdisperse discontinuous phase of the pharmaceutical agent. The first composition preferably further includes a non-fluorocarbon co-solvent in which the pharmaceutical agent is soluble. In one embodiment, the discontinuous phase that results upon mixing comprises the pharmaceutical agent and the co-solvent. In another, it consists essentially of the pharmaceutical agent, or it comprises a suspension of the pharmaceutical agent.

Other objects, features and advantages of the present invention will be apparent to those skilled in the art from a consideration of the following detailed description of preferred exemplary embodiments thereof.

DETAILED DESCRIPTION OF THE EXEMPLARY EMBODIMENTS

In a broad aspect, the stable high bioavailability pharmaceutical microdispersions of the present invention comprise a two phase system with a continuous liquid perfluorocarbon phase and a discontinuous lipophilic pharmaceutical phase. The discontinuous phase preferably forms spontaneously as a result of exceeding the solubility of the pharmaceutical in the continuous phase. Depending on whether the incorporated co-solvent is in the discontinuous phase, the form of the microdispersion may either be a reverse emulsion (co-solvent is present in the discontinuous phase) or a suspension (co-solvent is not present in the discontinuous phase). Unlike prior art fluorochemical delivery vehicles, the incorporation of lipophilic pharmaceutical agents in the homogeneous microdispersions of the present invention allows for their effective delivery to aqueous physiological target sites. Those skilled in the art will further appreciate that, due to the bacteriostatic, nonirritating, and in fact, soothing and lubricating properties of the fluorochemical microdispersions, the formulations of the present invention are extremely well-suited for use in applications where repeated or prolonged administration is required. Other aspects of the present invention are related to methods for forming the disclosed microdispersions and methods for their administration to a physiologic target site.

In order to appreciate the unique and unexpected characteristics of the present invention it must be emphasized that the formation of the stable, homogeneous microdispersions is related to the relative lipophilicity of the components rather than their absolute lipophilicity. That is, the lipophilicity of one component will influence the selection of the other components that are compatible with the invention. More particularly, the lipophilic fluorochemical used in the liquid carrier must be sufficiently lipophilic, when combined with at least one co-solvent, to incorporate the lipophilic pharmaceutical agent or agents of interest into a thermodynamically stable composition. This thermodynamically stable composition may be, but is not required to be, a molecular solution. Accordingly, the lipophilic fluorochemical selected will be influenced by the lipophilicity of the pharmaceutical agents that are to be incorporated. Similarly, the selection of the fluorochemical diluent used to effect the desired phase separation will be influenced by the choice of lipophilic fluorochemical used to incorporate the pharmaceutical agent in the thermodynamically stable composition. Any fluorochemical diluent sufficiently lipophobic to produce the desired microdispersion from the thermodynamically stable composition may be selected. In other words, when a lipophilic fluorochemical is used to incorporate the pharmaceutical agent, a more lipophilic diluent (but less lipophilic than the fluorochemical in the thermodynamically stable solution) may be used to initiate the phase separation. Conversely, when the fluorochemical used in the thermodynamically stable composition is relatively less lipophilic, the fluorochemical diluent required will generally be less lipophilic. Essentially, any combination of lipophilic fluorochemical and fluorochemical diluent that produces the desired microdispersion is considered by the inventors to constitute part of the present invention.

Although the scope of the invention is defined by the formation of the desired microdispersions, some indication of which components will operate in combination to produce the preferred results may be obtained from a comparison of their lipophilicity as determined by methods well known in the art. The lipophilicity of a compound can be related to several different parameters including the critical solution temperature in n-hexane (CSTH), the molar refraction ($R_m$) and the logarithm of the octanol-water partition coefficient (log $P_{o/w}$). While each of these methods are commonly used to determine the lipophilicity of different agents, certain methods are preferred for different classes of compounds. For instance, the lipophilicity of pharmaceutical compounds are typically measured and reported using the log of the octanol-water partition coefficient (log $P_{o/w}$). Conversely, the lipophilicity of liquid fluorochemicals can be generally related to the critical solution temperature in n-hexane (CSTH), and the molar refraction ($R_m$) methods with the CSTH standard being the more common of the two. For the purposes of describing the present invention this convention will be followed. Accordingly, for purposes of explanation only, exemplary lipophilicity values for pharmaceutical agents will be provided as determined by the octanol-water partition coefficient while exemplary lipophilicity values for liquid fluorochemicals will be provided as determined by using the molar refractivity and CSTH.

Those skilled in the art will appreciate that the critical solution temperature in n-hexane is defined to be the temperature at which an equivolume mixture of n-hexane and the substance to be measured form two immiscible liquid phases from a single liquid phase. The molar refraction is calculated by the following equation:

$$R_m = V_m(n^2-1)/(n^2+2) \qquad \text{Eq. 1}$$

where, $V_m$ and n are the molar volume and refractive index, respectively. Generally, for a class of compound, having the same number of carbons, the lower the value obtained, the more lipophilic the compound. For the purposes of this application the $R_m$ values were calculated using a computer model based on group contribution-additivity and quantum mechanical behaviour based on emperical observations. Accordingly, the values contained herein are estimates of lipophilicity offered for purposes of explanation only and in no way limit the scope of the invention.

Finally, the octanol-water partition coefficient (P o/w) is the ratio of the amounts of a substance that partition between equal volumes of octanol and water. That is, the lipophilic substance to be measured is transferred to an octanol/water mixture and the amount of substance in each phase is subsequently measured. As reported in the literature, the higher the value obtained, the more lipophilic the substance in question.

Due to the low polarizability of highly fluorinated compounds, the solubilities of nonfluorinated substances, including many lipophilic drugs, in fluorochemicals is very low. In order to incorporate pharmaceutically effective amounts of lipophilic agents in fluorochemicals, the fluorochemicals used must be relatively lipophilic in nature. The lipophilicity of fluorochemicals can be significantly increased by substituting fluorine atoms with more polarizable groups. Substituents which are particularly effective are polarizable halogens (i.e. Br, Cl, I) and hydrocarbon chains.

More particularly, lipophilic fluorochemicals, or combinations of lipophilic fluorochemicals which are capable of promoting the dissolution and incorporation of the selected lipophilic agent or agents into the thermodynamically stable compositions of the present invention are preferred. Exemplary lipophilic fluorochemicals which are particularly suited for use in the invention contain one or more nonfluorine halogen atoms (i.e. bromine, chlorine, iodine), or a hydrocarbon substituent group (i.e. —$C_2H_5$). In a preferred embodiment, the fluorochemical contains up to eight carbons. In a particularly preferred embodiment, the fluorochemical contains between four and six carbons. The molecular structures of the fluorochemicals used to form the thermodynamically stable composition may be linear, branched or contain cyclic structures. They may also be saturated, unsaturated or contain aromatic groups.

As discussed above, any lipophilic fluorochemical capable of incorporating the selected lipophilic pharmaceutical agent into a thermodynamically stable composition is compatible with the teachings herein and within the scope of the invention. That is, the lipophilic fluorochemicals which can be used in the current invention are defined by the selected lipophilic pharmaceutical agent. Yet, as an indication of which lipophilic fluorochemicals may be particularly beneficial, molar refractivity values and critical solution temperatures in n-hexane (CSTH) may be considered. Preferably the relatively lipophilic fluorochemicals used to incorporate the selected pharmaceutical agent will have molar refractivity values less than about 45 cm$^3$ or CSTH values of less than about 10° C. In particularly preferred embodiments, the relatively lipophilic perfluorchemicals will have molar refractivity values less than about 40 cm$^3$ or CSTH values of less than about −20° C. In one exemplary embodiment of the invention, the lipophilic fluorochemical is 1,4-dibromo-F-butane which has a molar reactivity value of approximately 36.68 cm$^3$. Table 1, immediately below, lists the molar refractivity values of this lipophilic fluorochemical and others which are compatible with the present invention.

TABLE 1

| Molar refractivity values for relatively lipophilic fluorochemicals | |
|---|---|
| Fluorochemical | Estimated Molar Refractivity ($R_m$) (cm3) |
| n-BrC$_4$F$_8$Br | 36.68 |
| n-C$_4$F$_9$ C$_4$H$_9$ | 40.59 |
| n-C$_4$F$_9$ C$_2$H$_5$ | 31.38 |
| n-ClC$_4$F$_8$Cl | 32.26 |

More particularly, exemplary lipophilic fluorochemicals which are contemplated for use in forming the thermodynamically stable compositions of the present invention include the halogenated fluorochemicals (i.e. $C_nF_{2n+1}X$, $XC_nF_{2n}X$, where n=3–8, X=Br, Cl or I), fluorocarbon-hydrocarbon diblock or triblock compounds (i.e. $C_nF_{2n+1}$-$C_mH_{2m+1}$, $C_nF_{2n+1}CH=CHC_mH_{2m+1}$, where n=2–8; m=2–6 or $C_pH_{2p+1}$—$_nF_{2n}$—$_mH_{2m+1}$, where p=1–6, m=1–6 and n=2–6), halogenated ethers or polyethers (i.e. $XC_nF_{2n}OC_mF_{2m}X$, $XCF_2OC_nF_{2n}OCF_2X$, where n, m=1–4, X=Br, Cl or I) and fluorocarbon-hydrocarbon ether diblocks or triblocks (i.e. $C_nF_{2n+1}$—O—$C_mH_{2m+1}$, where n=2–8; m=2–6 or $C_pH_{2p+1}$—O—$C_nF_{2n}$—O—$C_mH_{2m+1}$, where p=2–6, m=2–6 and n=2–8).

Fluorocarbon-hydrocarbon compounds and halogenated fluorocarbons containing other linkage groups, such as esters, thioesters, amines and amides are also suitable for use in forming the thermodynamically stable compositions of the present invention. Mixtures of fluorochemicals are also contemplated. Other suitable fluorochemicals may include the brominated perfluorocarbons, such as n-C$_4$F$_9$Br, 1-bromo-F-heptane (n-C$_7$F$_{15}$Br), and 1-bromo-F-hexane (n-C$_6$F$_{13}$Br). Also contemplated are fluorochemicals having nonfluorine substituents, such as perfluorooctyl chloride (n-C$_7$F$_{15}$Cl), 1, 6-dichloro-F-hexane (n-ClC$_6$F$_{12}$Cl), and 1, 4-dichloro-F-butane (n-ClC$_4$F$_8$Cl). 1, 4-dibromo-F-butane and 1,6-dibromo-F-hexane are particularly preferred.

In preferred embodiments, the relatively lipophilic fluorochemical will comprise less than about 50%, v/v, of the disclosed pharmaceutical microdispersions. Moreover, the preferred lipophilic fluorochemicals have vapor pressures sufficiently low to prevent significant liquid loss caused by evaporation during storage or delivery. More specifically, lipophilic fluorochemicals having ambient pressure boiling points greater than about 37° are preferred.

As detailed above, the diluent selected for each individual pharmaceutical microdispersion of the present invention is a fluorochemical that is less lipophilic than the fluorochemical included in the thermodynamically stable composition to be combined with that diluent. Accordingly, any physiologically acceptable fluorochemical diluent may be used for a particular microdispersion as long as it is capable of initiating the required phase separation. Generally, this means that the lipophilicity of the fluorochemical diluent will be less than the lipophilicity of the fluorochemical comprising the thermodynamically stable composition. The ability to use various fluorochemicals as diluents is particularly advantageous as they may be selected based on bio compatibility, to tailor certain characteristics of the microdispersion such as average particle size or continuous phase viscosity or it may be selected based on nontechnical constraints such as cost or availability. Biocompatible (preferred PFC's) include F-decalin, F-perhydrophenanthron, F-octane, F-tripropylamines, F-tributylamine, PFOB, F44E.

While the range of measured lipophilicity for diluent fluorochemicals is generally lower than the range of measured lipophilicity for fluorochemicals comprising the thermodynamically stable composition, there may be some overlap. For example, when a highly lipophilic fluorochemical is used to form the stable composition, a fluorochemical having some lipophilicity (but not as much as the highly lipophilic fluorochemical) may be used as a diluent to initiate the phase separation and produce the desired microdispersion. In another formulation it may be possible to use a fluorochemical having some lipophilicity to comprise the thermodynamically stable composition and use an extremely nonlipophilic fluorochemical to produce the microdispersion. Both microdispersions are within the scope of the present invention even though the same fluorochemical was used as a diluent in one case and to form the thermodynamically stable composition in the other case.

Nevertheless, as with the lipophilic fluorochemicals discussed above, the molar refractivity values and critical solution temperatures in n-hexane (CSTH) may be used to indicate which fluorochemicals are likely to be compatible with the invention. This is particularly true when the measured values are compared with the measured values of the lipophilic fluorochemical. Preferably the fluorochemical used to initiate the desired phase separation will have molar refractivity values greater than about 38 $cm^3$ or CSTH values of greater than about $-40°$ C. In particularly preferred embodiments, the diluent fluorochemicals will have molar refractivity values greater than about 45 $cm^3$ or CSTH values of greater than about 20° C. Table 2, immediately below, lists the molar refractivity values of fluorochemicals which are useful as diluents in the present invention.

TABLE 2

| Fluorochemical | Molar refractivity values for relatively nonlipophilic fluorochemicals |
|---|---|
| | Estimated Molar Refractivity ($R_m$) (cm3) |
| n-$C_8F_{17}Br$ | 50.210 |
| n-$C_7F_{15}Br$ | 44.90 |
| n-$C_6F_{13}Br$ | 39.59 |
| $C_4F_9CH=CH\ C_4F_9$ | 51.86 |
| n-$C_8F_{17}\ C_2H_5$ | 52.62 |
| n-$C_8F_{18}$ | 42.50 |
| n-$BrC_8F_{16}Br$ | 57.92 |
| n-$ClC_8F_{16}Cl$ | 53.50 |

Fluorochemicals useful as ethenes diluents in the present invention include bis(F-alkyl) such as $C_4F_9CH=CHC_4F_9$ (sometimes designated "F-44E"), i-$C_3F_9CH=CHC_6F_{13}$ ("F-i36E"), and $C_6F_{13}CH=CHC_6F_{13}$ ("F-66E"); cyclic fluorochemicals, such as C10F18 ("F-decalin", "perfluorodecalin" or "FDC"), F-adamantane, ("FA"), F-methyladamantane ("FMA"), F-1,3 -dimethyladamantane ("FDMA"), F-di-or F-trimethylbicyclo[3,3,1]nonane ("nonane"); perfluorinated amines, such as F-tripropylamine ("FTPA") and F-tributylamine ("FTBA"), F-4-methyloctahydroquinolizine ("FMOQ"), F-N-methyl-decahydroisoquinoline ("FMIQ"), F-N-methyldecahydroquinoline ("FHQ"), F-N-cyclohexylpurrolidine ("FCHP") and F-2-butyltetrahydrofuran ("FC-75" or "FC-77").

Other fluorochemicals which may be used as diluents include brominated fluorochemicals, such as 1-bromo-heptadecafluoro-octane ($C_8F_{17}Br$, sometimes designated perfluorooctylbromide or "PFOB"), 1-bromopentadecafluoroheptane ($C_7F_{15}Br$), and 1-bromotridecafluorohexane ($C_6F_{13}Br$, sometimes known as perfluorohexylbromide or "PFHB"). Other brominated fluorochemicals are disclosed in U.S. Pat. No. 3,975,512 to Long. Also contemplated are fluorochemicals having non-fluorine substituents, such as perfluorooctyl chloride, perfluorooctyl hydride, and similar compounds having different numbers of carbon atoms.

Additional fluorochemicals contemplated in accordance with this invention include perfluoroalkylated ethers or polyethers, such as $(CF_3)_2CFO(CF_2CF_2)_2OCF\ (CF_2)_2$, $(CF_3)_2CFO-(CF_2CF_2)_3OCF(CFRM101_3)_2$, $(CF_3)_2CFO\ (CF_2CF_2)_xF$, where x=1–6 $(CF_3)_2CFO\ (CF_2CF_2)_2F$, $(C_6F_{13})_2O$. Further, fluorochemical-hydrocarbon compounds, such as, for example compounds having the general formula $C_nF_{2n+1}-_nF_{2n'+1}$, $C_nF_{2n+1}OC_nF_{2n'+1}$, or $C_nF_{2n+1}CH=CHC_n'F_{2n'+1}$, where n and n' are the same or different and are from about 1 to about 10 (so long as the compound is a liquid at room temperature). Such compounds, for example, include $C_8F_{17}C_2H_5$ and $C_6F_{13}CH=CHC_6H_{13}$. It will be appreciated that esters, thioethers, other variously modified mixed fluorochemical-hydrocarbon compounds and fluorocarbons are also encompassed within the broad definition of fluorochemical suitable for use in the present invention. In preferred embodiments the diluent will comprise greater than about 50% v/v of the disclosed microdispersions. Mixtures of fluorochemicals are also contemplated. Additional fluorochemicals not listed here, but having those properties described in this disclosure that would lend themselves to the formation of microdispersions are additionally contemplated.

As previously mentioned some fluorochemicals have relatively high vapor pressures and correspondingly low boiling points which render them less suitable for use in the present invention. In particular, such volatile compounds are less useful for partial liquid breathing and pulmonary administration of drugs. These include 1-bromotridecafluorohexane ($C_6F_{13}Br$) and F-2-butyltetrahyddrofuran ("FC-75" or "RM101"). More specifically, lipophilic fluorochemicals having ambient pressure boiling points greater than 37° are particularly advantageous.

As pulmonary delivery of drugs is an important aspect of the present invention the fluorochemicals chosen as diluent (and to a lesser extent as the lipophilic fluorochemical) should preferably have functional characteristics that would permit its use temporarily as a lung surfactant, for oxygen delivery, in removal of material from the interior of the lung, or for inflation of collapsed portions of the lung. Fluorochemicals are biocompatible and most are amenable to sterilization techniques. For example, they can be heat-sterilized (such as by autoclaving) or sterilized by radiation. In addition, sterilization by ultrafiltration is also contemplated.

In one embodiment of the invention, the pharmaceutical is first provided in a continuous phase with a non-fluorocarbon first liquid. Such a liquid is preferably a solvent for the pharmaceutical, and may be selected from the group consisting of ethers, alcohols, alkyl sulfoxides and combinations thereof. Liquids which are particularly suitable for use with the present invention are short chain alcohols (i.e. carbon chain length ≦4 carbons) or an alkyl sulfoxide such as dimethylsulfoxide. In a particularly preferred embodiment this co-solvent is ethanol. In this embodiment, the microdispersion is formed by adding a second liquid, miscible in the first, but in which the pharmaceutical is less soluble. Such second liquids can include lipophilic and nonlipophilic fluorocarbons of the type described herein, oils, lipids, and even water.

In normal physiological systems, surfactants function to decrease the surface tension of the alveolar tissue. The lung surfactant is found in a water-continuous fluid lining the alveolus. Typically, the surface tension in the absence of lung surfactant is ca. 70 dynes/cm decreasing to near 0 dynes/cm in the presence of lung surfactant. Fluorochemicals have low surface tension values (typically in the range of 20 dynes/cm) and have the added benefit of dissolving extremely large quantities of gases such as oxygen and carbon dioxide. Perfluorochemicals are suited for this use, and brominated fluorochemicals are particularly preferred. Moreover, the low surface tension imparted by the fluorochemical continuous phase of the present invention may increase the bioavailability of the incorporated pharmaceutical agent and thereby increase its efficacy.

Although reduction in surface tension is an important parameter in judging fluorochemicals and perfluorochemicals as pulmonary delivery vehicle, or for use in partial liquid breathing, a novel and non-obvious characteristic of some fluorochemicals is their apparent ability to spread over the entire respiratory membrane. Like the ability of fluorochemicals to reduce surface tension, the ability of some fluorochemicals to spread evenly and effectively over lung surfaces may increase the increase bioavailability, and hence the uptake of the incorporated pharmaceutical agent.

The total surface area of the respiratory membrane is extremely large (ca. 160 square meters for an adult). Thus, an effective fluorochemical for partial liquid breathing and concurrent drug delivery should be able to cover the lung surfaces with relatively little volume.

The ability of a given substance to cover a measured surface area can be described by its spreading coefficient. The oil-on-water spreading coefficients for fluorochemicals can be expressed by the following equation:

$$S\ (o\ on\ w)=\gamma w/a-(\gamma w/o+\gamma o/a) \qquad \text{Eq. 2}$$

Where S (o on w) represents the spreading coefficient; γ=interfacial tension; w/a=water/air; w/o=water/oil; and o/a=oil/air.

If the fluorochemical exhibits a positive spreading coefficient, then it will spread over the surface of the respiratory membrane spontaneously. Fluorochemicals having spreading coefficients of at least one, such as perfluorooctylbromide, are particularly preferred as diluents for microdispersions to be used for pulmonary drug administration. Of course, it must be emphasized that fluorochemicals with lower coefficients may be used to formulate microdispersions in accordance with the present invention and used for the effective administration of drugs including pulmonary administration. In addition to enhancing the bioavailability of the incorporated pharmaceutical agent, adequate coverage of the lung surface is beneficial for restoring oxygen and carbon dioxide transfer and for lubricating the lung surfaces to minimize further pulmonary trauma. In this respect fluorochemicals useful as diluents are generally able to promote gas exchange. This is also true of the lipophilic fluorochemicals previously listed. Accordingly, in preferred embodiments, the microdispersions of the present invention will be enriched through the introduction of a physiologically acceptable gas.

In addition to the fluorochemicals used in the present invention, the microdispersions preferably contain at least one nonfluorinated co-solvent to facilitate the incorporation of the lipophilic pharmaceutical agent in the thermodynamically stable pharmaceutical composition. Preferably this co-solvent is entirely miscible with the selected lipophilic fluorochemical and comprises up to about 75%, v/v of the thermodynamically stable composition. In a most preferred embodiment, the concentration of the nonfluorinated co-solvent comprises up to about 50%, v/v, of the thermodynamically stable composition.

Exemplary embodiments of the invention preferably include a co-solvent selected from the group consisting of ethers, alcohols, alkyl sulfoxides and combinations thereof. Co-solvents which are particularly suitable for use with the present invention are short chain alcohols (i.e. carbon chain length≦4 carbons) or an alkyl sulfoxide such as dimethylsulfoxide. In a particularly preferred embodiment this co-solvent is ethanol.

As previously discussed, the concentration of the nonfluorinated co-solvent is an important factor in determining whether the microdispersion is generated as a suspension (a solid discontinuous phase) or as an emulsion (a liquid dispersed in another liquid discontinuous phase). Generally, a suspension will be formed when the concentration of the co-solvent in the pharmaceutical microdispersion does not exceed its solubility in the same. In this case the co-solvent remains in the fluorochemical continuous phase as the lipophilic pharmaceutical compound is forced out through combination with the diluent. Conversely, when the concentration of the co-solvent exceeds its solubility in the pharmaceutical microdispersion following addition of the diluent, the insoluble volume will be forced into the discontinuous phase with the lipophilic pharmaceutical agent thereby forming an emulsion. The inherent ability to easily alter the form of the microdispersion depending on the intended administration route is a major advantage of the invention allowing the attenuation of drug delivery profiles and dosing regimes.

As alluded to previously, the microdispersions of the present invention may also comprise one or more additives which are present in the discontinuous pharmaceutical phase, in the fluorochemical continuous phase, in both of these phases, or at the interface between the phases. Among other additives, one or more fluorinated or nonfluorinated surfactants may be present in the thermodynamically stable composition. Surfactants are amphiphilic molecules which contain both a hydrophilic "head group" and a lipophilic "tail." The surfactant typically forms a monomolecular layer at liquid-liquid and liquid-solid interfaces, lowering the interfacial tension. This lowering of interfacial tension significantly reduces the coarsening of the microdispersion and may sharply increase the shelf-life. Among the surfactants contemplated for use in the present invention are fluorinated and nonfluorinated phospholipids which include, phosphatidylethanolamines, phosphatidic acids and phosphatidylcholines. Other emulsifying agents suitable for use in this invention include, but are not limited to fluorinated and non fluorinated glyceroglycolipids, egg yolk lecithins, salts of fatty acids, ether linked lipids and diacylphosphates.

The pharmaceutical microdispersions of the present invention are capable of delivering any desired pharmaceutical agent that may be incorporated in the thermodynamically stable composition and forced into a discontinuous phase through the addition of a fluorochemical diluent. As used herein, the term pharmaceutical agent is defined to mean any therapeutic or diagnostic compound or composition which may be administered to an animal. Preferred pharmaceutical agents include nonionichydrophilic drugs with solubility in ethanol and lipophilic drugs. Most preferably, the incorporated pharmaceutical agents are lipophilic agents.

Preferably, the pharmaceutical microdispersions of the present invention incorporate less than about 10% w/v of a therapeutic or diagnostic agent. The precise amount of pharmaceutical agent incorporated in the microdispersions of the present invention is dependent upon the agent of choice, the required dose, and the form of the drug actually incorporated in the microdispersion. Those skilled in the art will appreciate that such determinations may be made by using well-known techniques in combination with the teachings of the present invention.

Preferred pharmaceutical agents comprise respiratory agents, antibiotics, antivirals, mydriatics, antiglaucomas, anti-inflammatories, antihistamines, antineoplastics, anesthetics, ophthalmic agents, cardiovascular agents, active principles, nucleic acids, genetic material, immunoactive agents, imaging agents, immunosuppressive agents, gastrointestinal agents and combinations thereof. Further exemplary embodiments of the present invention comprise anti-inflammatory agents such as the glucocorticosteroids (i.e. cortisone, prednisone, prednisolone, dexamethasone, betamethasone, Beclomethasone diproprionate, Triamcinolone acetonide, Flunisolide), xanthines (i.e. theophylline, caffeine), chemotherapeutics (i.e. cyclophosphamide, lomustine, methotrexate, cisplatin, taxane derivatives), antibiotics (i.e. aminoglycosides, penicillins, cephalosporins, macolides, quinolones, tetracyclines, chloramphenicol), bronchodilators such as the $B_2$-agonists (i.e. adrenaline, isoprenaline, salmeterol, albuterol, salbutamol, terbutaline, formoterol) and surfactants. Still other exemplary embodiments include α/β adrenergic blockers (i.e. Normodyne™, Trandate™), angiotensin converting enzyme inhibitors (i.e. Vasotec™), antiarrhythmics, beta blockers, calcium channel blockers, inotropic agents, vasodilators, vasopressors, anesthetics (i.e. morphine) and ophthalmic agents (i.e. polymyxin B, Neomycin, Gramicidin).

Most preferred agents include glucocorticosteroids, taxane derivatives (i.e. Taxol™, Taxotere™) and the base forms of drugs typically administered as the salt derivative (i.e. Gentimicin, Ciprofloxacin). In accordance with the present invention, those skilled in the art will appreciate that various forms of these compounds may be used to modify the therapeutic index of the pharmaceutically active agents.

Similar to the fluorochemicals discussed above, the selection of lipophilic pharmaceutical agents is limited only by the ability to incorporate them in the desired microdispersions as disclosed in the present invention. Yet, some indication as to the compatibility of an individual pharmaceutical agent may be derived from the measured value of its lipophilicity. Unlike the fluorochemical components of the present invention, the convention is to measure and report the lipophilicity of a pharmaceutical compound using the log of the octanol/water partition coefficient (Log $P_{o/w}$). In this system increasing lipophilicity corresponds to higher Log $P_{o/w}$ values. Preferably the lipophilic agents incorporated in the present invention will have a Log $P_{o/w}$ greater than about 0.5. More preferably the pharmaceutical agents will have a Log $P_{o/w}$ greater than about 2.0. As those skilled in the art will appreciate, values such as these indicate that a compound has limited solubility in an aqueous environment. The octanol/water partition coefficients of several exemplary lipophilic pharmaceutical agents compatible with the teachings of the present invention, are reproduced below in Table 3.

TABLE 3

Octanol/water Partition coefficients (Po/w) of various drugs

| Drug Substance | $P_{o/w}$ | Log $P_{o/w}$ |
|---|---|---|
| $^{14}$C-anthracene$^1$ | $3.16 \times 10^4$ | 4.5 |
| $^{14}$C-bunolol$^1$ | $2.51 \times 10^2$ | 2.4 |
| $^{14}$C-cimetidine$^1$ | 2.51 | 0.4 |
| $^{14}$C-hexamethylene lauramide$^1$ | $2.00 \times 10^7$ | 7.3 |
| $^{14}$C-padimate-o$^1$ | $3.98 \times 10^6$ | 6.6 |
| $^{14}$C-progesterone$^1$ | $7.9 \times 10^3$ | 3.9 |
| $^{14}$C-testosterone$^1$ | $2.00 \times 10^3$ | 3.3 |
| $^3$H-clonidine$^1$ | 25.1 | 1.4 |
| $^3$H-diethylstilbesterol$^1$ | $1.26 \times 10^5$ | 5.1 |
| $^3$H-fluorometholone$^1$ | $1.26 \times 10^2$ | 2.1 |
| $^3$H-parsol 1789$^1$ | $5.0 \times 10^6$ | 6.7 |
| valeryl acyclovir$^2$ | 2.01 | 0.30* |
| hexanoyl acyclovir$^2$ | 8.58 | 0.93* |
| lidocaine$^3$ | 2.88 | 0.46 |
| bupivacaine$^3$ | 28.2 | 1.45 |
| tetracaine$^3$ | 79.4 | 1.90 |
| halothane$^4$ | $2.00 \times 10^2$ | 2.30 |
| ampicillin$^4$ | 11.5 | 1.06 |
| oxazepam$^4$ | $1.78 \times 10^2$ | 2.25 |
| pentazocin$^5$ | 150 | 2.18* |
| nitrazepam$^5$ | 162 | 2.21* |
| haloperidol$^5$ | 485 | 2.69* |
| biperiden$^5$ | 678 | 2.83* |
| diazepam$^5$ | 970 | 2.99* |
| promethazine$^5$ | $1.27 \times 10^3$ | 3.10* |
| trihexyphenidyl$^5$ | $1.47 \times 10^3$ | 3.17* |
| chlorpromazine$^5$ | $1.90 \times 10^3$ | 3.28* |
| clotiazepam$^5$ | $3.06 \times 10^3$ | 3.49* |
| clomipramine$^5$ | $3.80 \times 10^3$ | 3.58* |

$^1$Tang-Liu, D. D. -S., Richman, J. B. and Liu, S. S., J. Ocul. Pharmac., 1992, 8, 267.
$^2$Hughes, P. M. and Mitra, A. K. , J. Ocul. Pharmac. , 1993, 9, 299.
$^3$Hageluken, A., Grunbaum, L., Nurnberg, B., Harhammer, R., Schumack, W. and Seifert, R. , Bicchem. Pharmac., 1994, 47, 1789.
$^4$Moriguchi, I. , Hirono, S., Liu, Q., Nakagome, I. and Matsuchita, Y., Chem. Pharm. Bull., 1992, 40, 127.
$^5$Yokogawa, K. , Nakashima, E., Ishizaki, J. , Maeda, H., Nagano, T. and Ichimura, F., Pharm. Res. 1990, 7, 691.
*in octanol/pH 7.4 isotonic phosphate buffer at 37° C.

Because the microdispersions of the present invention are uniquely suited for use in a wide variety of physiological applications such as ocular, oral, pulmonary, rectal, subcutaneous, intramuscular, intraperitoneal, nasal, vaginal, or aural administration of medicaments or diagnostic compounds, a wide variety of pharmaceutical agents may be incorporated therein. Accordingly, the foregoing list of pharmaceutical agents is exemplary only and not intended to be limiting.

Another unique advantage provided by the microdispersions of the present invention is the ability to use the free base form of the incorporated pharmaceutical agent rather than its less efficacious salt form. That is, the efficay of lipophilic forms of drugs have been shown in many instances to be more potient than the less lipophilic forms of the drug, i.e. the salts. The nonreactive nature of the fluorochemical microdispersions allow the incorporation of particularly efficacious base forms of the selected pharmaceutical agent. As those skilled in the art will appreciate, the use of these more potent drug forms enhances the bioavailability of the incorporated pharmaceutical agent and reduces the dosages which must be administered.

It will also be appreciated by those skilled in the art that the proper amount of pharmaceutical and the timing of the dosages may be determined for the formulations in accordance with already-existing information and without undue experimentation.

Note that, the fluorochemical microdispersions can be administered via several different routes, depending upon the indication to be treated. For example, intranasal or intrapulmonary administration (i.e. endotracheal tube or pulmonary catheter), aerosolization or nebulization is contemplated for the treatment of respiratory or systemic disorders. An example would include the treatment of lung cancer or other systemic cancers with taxane derivatives by the pulmonary administration of these drugs. Due to its low aqueous solubility paclitaxel (i.e. Taxol) is formulated in a mixture of polyoxyethylated castor oil and ethanol Bristo-Myers Squibb) which is intended for intravenous administration. In addition to manifestations of hypersensitivity associated with the delivery vehicle itself (i.e. bronchospasm and hypotension) other systemic toxicities associated with paclitaxel such as, cardiac toxicity and neurotoxicity limit the potential usefulness of this drug (Arabic, S. G., Christian, M. C., Fisherman, J. S., Cazenave, L. A., Sarosy, G., Suffness, M., Adams, J., Canetta, R., Cole, K. E., and Friedman, M. A., J. Natl. Canc. Inst. Monogr. 1993, No. 15, 11.) The administration of paclitaxel via the intrapulmonary route in the form of a fluorochemical suspension could significantly improve the safety profile of the drug by eliminating the use of biologically active delivery vehicles and by reducing the concentration of the drug in the circulation required for drug efficacy. Intraperitoneal, subcutaneous and ocular administration are also contemplated. The fluorochemical microdispersions of the invention may also be used to deliver therapeutic and diagnostic agents to the gastrointestinal tract by the oral route of administration. A contemplated example would be the delivery of antibiotics to the lining of the gastrointestinal tract in the treatment of *Heliobacter pylori* infections. *H. pylori* has been implicated in the cause of gastric ulcers and stomach cancer. Antibiotics effective in the treatment of *H. pylori* infections could be administered in the form of a submicron sized fluorochemical suspensions.

As previously discussed, the microdispersions of the present invention may be prepared by incorporating a lipophilic pharmaceutical agent into a thermodynamically stable composition comprising at least one lipophilic fluorochemical and at least one nonfluorinated co-solvent. Depending on the presence of optional additives such as surfactants, the thermodynamically stable composition may or may not be a molecular solution. In any case, once the thermodynamically stable composition is formed it may be combined with the fluorochemical diluent. Generally the diluent is of greater volume than the thermodynamically stable composition. As the combination equilibrates, a phase separation is initiated by the lowered lipophilicity of the entire system, which causes the lipophilic pharmaceutical agent and possibly a portion of the co-solvent to be forced into a discontinuous phase, forming a microdispersion.

The discontinuous phase may be in the form of a reverse emulsion or a suspension. In either case, the substantially homogeneous microdispersions of the present invention may comprise extremely small particulates having an average diameter on the order of tens of nanometers. As used herein, the terms "particles" or "particulates" will refer to the discontinuous phase of the microdispersions whether that phase is liquid or solid. In the present invention, such small, evenly distributed particles greatly increase the bioavailability of the incorporated pharmaceutical agents at the physiological target site due to their relatively large surface area and correspondingly rapid dissolution time. Conversely, by altering the microdispersion components, reaction conditions, or time for which the reaction is allowed to proceed, the incorporated particulates may be grown to be as large as a few microns. Those skilled in the art will appreciate that the ability to control the incorporated particle size may be used to attenuate and extend drug delivery profiles to optimize dosing regimes. Preferably, the average particle diameter will be less than about 3 µm, and more preferably less than about 1 µm. In many preferred embodiments, the average particle diameter may be as small as a few nanometers, e.g., 2,3,4,5,7, or 10 nm.

As discussed previously, the reverse emulsions of the present invention comprise a discontinuous co-solvent/pharmaceutical phase and a perfluorochemical continuous phase. As with the suspensions, the reverse emulsions of the present invention may incorporate fluorinated or nonfluorinated surfactants to promote stability. The amount of surfactant employed is generally less than about 10% (w/v) of the total volume. The emulsion may be formed following the combination of the diluent and the thermodynamically stable composition using procedures well known in the art. For example, the reverse emulsions of the invention are typically prepared by emulsifying the formulation by conventional homogenization such as, for example, microfluidization, sonication or homogenization under pressure.

Both the reverse emulsions and suspensions of the present invention may be sterilized, for example, by irradiation or by filtration.

The high bioavailability pharmaceutical formulations of the present invention may advantageously be supplied to the physician in a sterile prepackaged form. More particularly, the formulations may be supplied as stable, preformed microdispersions ready for administration or as separate, ready to mix components. Typically, when supplied as components, the fluorochemical diluent will be packaged separately from the thermodynamically stable pharmaceutical composition. The microdispersion may then be formed at any time prior to use by simply combining the contents of each container.

The following nonlimiting examples of various exemplary formulations of the present invention illustrate exemplary methods for the their formation and resultant characteristics. For purposes of clarity in the following examples, the thermodynamically stable composition of the invention will be referred to as "Composition 1."

In order to illustrate the advantages of the present invention and demonstrate its widespread applicability, several lipophilic pharmaceutical agents were used to form pharmaceutical suspensions as described above. Each size microdispersion produced was assayed for particle distribution.

EXAMPLE 1

Preparation of a Suspension of Prednisone in a Fluorochemical

Three milliliters of the following fluorochemical continuous suspension was prepared:
Composition 1 0.38%, w/v, Prednisone (Sigma Chemical Co.) was dissolved into a solution composed of 1, 4-dibromo-F-butane (50%,v/v; Exfluor, Austin, Tex.) and NF grade ethyl alcohol (50%,v/v; Spectrum Chemical Co). Fluorochemical Diluent: perfluorooctylbromide (Atochem, France).

An aliquot of composition 1 (60 μL) was injected with a syringe into a sample of perfluorooctylbromide (PFOB; 3 mL) contained in a 12×100 mm test tube. The tube was capped and the contents gently mixed by inverting the tube. An opalescent submicron sized drug in fluorocarbon suspension was obtained. The particle size distribution of the dispersions was measured using photon correlation spectroscopy (PCS) on a Nicomp 270 photon correlation spectrophotometer (Pacific Scientific). The resulting drug dispersion had an average particle diameter of 60±42 nm.

EXAMPLE 2

Preparation of a Suspension of Paclitaxel In Fluorochemical

Three milliliters of the following fluorochemical continuous suspension was prepared:
Composition 1: 0.40% w/v of paclitaxel (Sigma Chemical Co.) was dissolved into a solution composed of 1,4-dibromo-F-butane (50%,v/v; Exfluor, Austin, Tex.) and NF grade ethyl alcohol (50%,v/v; Spectrum Chemical Co.). Fluorochemical Diluent: Perfluorooctylbromide (Atochem, France).

An aliquot of composition 1 (60 μL) was injected with a syringe into a sample of perfluorooctylbromide (PFOB; 3 mL) contained in a 12×100 mm test tube. The tube was capped and the contents gently mixed by inverting the tube. An opalescent submicron sized drug in fluorocarbon suspension was obtained. The particle size distribution of the dispersions was measured using photon correlation spectroscopy (PCS) on a Nicomp 270 photon correlation spectrophotometer (Pacific Scientific). The resulting drug dispersion had an average particle diameter of 50±32 nm.

EXAMPLE 3

Preparation of a Suspension of Prednisolone in a Fluorochemical

Three milliliters of the following fluorochemical continuous suspension was prepared:
Composition 1: 0.38%, w/v, Prednisolone (Sigma Chemical Co.) was dissolved into a solution composed of 1, 4-dibromo-F-butane (80%,v/v; Exfluor, Austin, Tex.) and NF grade ethyl alcohol (20%,v/v; Spectrum Chemical Co.). Fluorochemical Diluent: Perfluorooctylbromide (Atochem, France An aliquot of composition 1 (60 μL) was injected with a syringe into a sample of perfluorooctylbromide (PFOB; 3 mL) contained in a 12×100 mm test tube. The tube was capped and the contents gently mixed by inverting the tube. An opalescent submicron sized drug in fluorocarbon suspension was obtained. The particle size distribution of the dispersions was measured using photon correlation spectroscopy (PCS) on a Nicomp 270 photon correlation spectrophotometer (Pacific Scientific). The resulting drug dispersion had an average particle diameter of 57±32 nm.

EXAMPLE 4

Preparation of a Suspension of Diazepam in a Fluorochemical

Three milliliters of the following fluorochemical continuous suspension was prepared:

Composition 1: 0.38%, w/v, Diazepam (Sigma Chemical Co.) was dissolved into a solution composed of 1,4-dibromo-F-butane (90%,v/v; Exfluor, Austin, Tex.) and NF grade ethyl alcohol (10%,v/v; Spectrum Chemical Co.). Fluorochemical Diluent: Perfluorooctylbromide (Atochem, France).

An aliquot of composition 1 (180 μL) was injected with a syringe into a sample of perfluorooctylbromide (PFOB; 3 mL) contained in a 12×100 mm test tube. The tube was capped and the contents gently mixed by inverting the tube. An opalescent submicron sized drug in fluorocarbon suspension was obtained. The particle size distribution of the dispersion was measured using photon correlation spectroscopy (PCS) on a Nicomp 270 photon correlation spectrophotometer (Pacific Scientific). The resulting drug dispersion had an average particle diameter of 65±28 nm.

The foregoing examples demonstrate the reproducibility and applicability of the present invention to a variety of lipophilic pharmaceutical agents. It is important to note that in each of the examples described above a substantially homogeneous microdispersion was formed without extensive mixing or complicated processing equipment. Moreover, the uniformity of the particle distribution size and homogeneity of the suspension are superior to suspensions formed using conventional methods of adding dried powders to the continuous phase. In addition, the particulate size is extremely small allowing for rapid dissolution in the aqueous environment of the target site.

Further studies were performed to determine the importance of co-solvent concentration on particulate size.

EXAMPLE 5

Effect Of Ethyl Alcohol Concentration On Particle Size

A series of prednisone in PFOB suspensions was prepared to evaluate the effect of the ethyl alcohol concentration on particle size distribution. The sample preparation and particle size analysis are described in Example 1 with the only difference being the relative concentrations of 1,4-dibromo-F-butane and ethanol in composition 1. The solution composition and particle size distribution results are shown in the Table 4 directly below.

TABLE 4

The effect of ethyl alcohol concentration on mean drug particle diameter.

| Ethyl Alcohol % v/v in Solution 1 | Concentration of Prednisone in Composition 1 (%, w/v) | Microliters of Composition 1 injected into PFOB (3 mL) | Mean Particle Diameter (nm) | Standard Deviation (nm) |
|---|---|---|---|---|
| 10 | 0.17 | 130 | 60 | 35 |
| 20 | 0.22 | 108 | 50 | 25 |
| 50 | 0.38 | 60 | 60 | 42 |
| 70 | 0.49 | 46 | 300 | 950 |

The prednisone particle size distributions in the final dispersion were not significantly different for ethyl alcohol concentrations in Composition 1 up to 50%, v/v. A significant increase in mean particle size was observed for the suspension prepared with the 70%, v/v, ethyl alcohol drug containing solution.

While not wishing to be limited by any one theory of operation, it is believed that the observed results may be explained as follows. Once nuclei form in a supersaturated solution, they begin to grow by accretion and the concentration of the dissolved solute decreases. Therefore, there is a competition for material between the process of nucleation and of crystal growth and more rapid nucleation results in smaller particles. The concentrations of prednisone in the solutions containing smaller amounts of ethanol are much closer to their maximum solubilities in the lipophilic fluorochemical so that when Composition 1 is mixed with Fluorochemical Diluent, the drug containing solution does not have to diffuse as much to achieve supersaturation. As a result, the nucleation rates are faster and the particle sizes smaller when compared to the solution containing high concentrations of ethanol. By making the concentration of the lipophilic pharmaceutical agent in the thermodynamically stable composition close to its solubility limit, it should be possible to further reduce the average particle size and increase bioavailability. In any case the forgoing example demonstrates an abilty to control the size of the particulates produced to optimize the efficacy of the incorporated drug.

The following study was conducted to illustrate the compatibility of different co-solvents with the teachings of the present invention.

EXAMPLE 6

The Use of Dimethyl Sulfoxide as a Co-solvent in the Preparation of Prednisone Suspension in Fluorochemical Three milliliters of the following fluorochemical suspension was prepared:
Composition 1: 0.38%, w/v, Prednisone (Sigma Chemical Co.) was dissolved in a solution composed of 1,4-dibromo-F-butane (75%,v/v; Exfluor, Austin, Tex.) and NF grade ethyl alcohol (20%,v/v; Spectrum Chemical Co) and dimethyl sulfoxide (5%, v/v; Aldrich Chemical Co.).
Fluorochemical Diluent: Perfluorooctylbromide (Atochem, France).

An aliquot of composition 1 (60 µL) was injected with a syringe into a sample of perfluorooctylbromide (PFOB; 3 mL) contained in a 12×100 mm test tube. The tube was capped and the contents gently mixed by inverting the tube. An opalescent submicron sized drug in fluorocarbon suspension was obtained. The particle size distribution of the dispersions was measured using photon correlation spectroscopy (PCS) on a Nicomp 270 photon correlation spectrophotometer (Pacific Scientific). The resulting drug dispersion had an average particle diameter of 41±38 nm.

This experiment demonstrates that, in accordance with the teachings herein, different co-solvents or combinations thereof may be used to produce the high bioavailability microdispersions of submicron particles. Similarly the experiment described below demonstrates the ability to use different perfluorochemical diluents.

EXAMPLE 7

The Preparation of Prednisone Microdispersions in Various Fluorochemical Diluents An aliquot of composition 1 (60 µL) as prepared in example 1 was injected with a syringe into different fluorochemical diluents (3 mL) contained in 12×100 mm test tubes. The tubes were capped and the contents gently mixed by inverting the tubes. Opalescent submicron sized drug in fluorocarbon suspensions were obtained. The particle size distributions of the dispersions were measured using photon correlation spectroscopy (PCS) on a Nicomp 270 photon correlation spectrophotometer (Pacific Scientific). All of the fluorochemical delivery vehicles tested produced submicron sized fluorochemical continuous suspensions. The results are summarized in the table below.

TABLE 5

Prednisone Suspension Particle Size in Different Fluorochemical Diluents

| Fluorocarbon | mean particle diameter (nm) | standard deviation (nm) |
|---|---|---|
| n-$C_6F_{13}Br$ | 51 | 26 |
| n-$C_7F_{15}Br$ | 50 | 26 |
| n-$C_8F_{17}$ $C_2H_5$ | 71 | 67 |
| n-$C_8F_{17}Br$ | 60 | 42 |

As may be seen from the table above, effective suspensions of the present invention may be formed using various fluorochemical diluents. As such different diluents may be selected based on technical and nontechnical criteria such as gas transport abilities, viscosity and cost. This allows the formulations to easily be tailored to adapt to different situations.

In addition to the suspensions discussed in the examples above, the microdispersions may be formed as emulsions as evidenced by the example presented below.

EXAMPLE 8a

Preparation of Surfactantless Prednisone Containing Emulsions

Three milliliters of the following submicron sized fluorochemical continuous emulsion was prepared:
Composition 1: 0.49 %, w/v, Prednisone (Sigma Chemical Co.) was dissolved into a solution composed of 1,4-dibromo-F-butane (70%,v/v; Exfluor, Austin, Tex.) and NF grade ethyl alcohol (30%,v/v; Spectrum Chemical Co).

An aliquot of composition 1 (60 µL) was injected with a syringe into different fluorochemical diluents (3 mL) contained in 12×100 mm test tubes. The tubes were capped and submerged in a sonicator bath (Branson Model 3200) for 5 seconds to obtain a milky dispersion in fluorochemical continuous media. The particle size distributions of the dispersions were measured using photon correlation spectroscopy (PCS) on a Nicomp 270 photon correlation spectrophotometer (Pacific Scientific). The results are summarized in the Table 6 below.

TABLE 6

Mean Particle Diameter for Fluorochemical Continuous Pharmaceutical Emulsions

| Fluorochemical | mean particle diameter (nm) | standard deviation (nm) |
|---|---|---|
| F-decalin | 88 | 243 |
| n-$C_8F_{18}$ | 52 | 34 |
| F-tributylamine | 71 | 315 |

This data shows that liquid particles on the order of nanometers may easily be formed using the techniques disclosed herein. Those skilled in the art will appreciate that such emulsions will significantly increase the bioavailability of the incorporated pharmaceutical agent. It is important to note that while the emulsions were formed without a surfactant, similar results could be obtained with the inclusion of numerous fluorinated or nonfluorinated surfactants.

EXAMPLE 8b

The Use Of Dimethyl Sulfoxide In The Preparation Of Surfactantless Drug Containing Emulsions Three milliliters of the following submicron sized fluorochemical continuous emulsion was prepared:

Composition 1: 2.4%, w/v, Prednisone (Sigma Chemical Co.) was dissolved into a solution composed of dimethyl sulfoxide (50%, v/v; Aldrich Chemical Co.) and NF grade ethyl alcohol (50% ,v/v; Spectrum Chemical Co).

An aliquot of composition 1 (30 µL) was injected with a syringe into different fluorochemical delivery vehicles (3 mL) contained in 12×100 mm test tubes. The tubes were capped and submerged in a sonicator bath (Branson Model 3200) for 5 seconds. A milky emulsion in fluorochemical continuous media was obtained. The particle size distributions of the dispersions were measured using photon correlation spectroscopy (PCS) on a Nicomp 270 photon correlation spectrophotometer (Pacific Scientific). The results are summarized in the table below.

TABLE 7

| Mean particle diameters for fluorochemical continuous emulsions | | |
|---|---|---|
| Fluorocarbon | mean particle diameter (nm) | standard deviation (nm) |
| $n$-$C_8F_{17}$ $C_2H_5$ | 169 | 243 |
| $n$-$C_8F_{17}Br$ | 178 | 136 |
| $C_4F_9CH{=}CH$ $C_4F_9$ | 85 | 250 |

As with the suspensions, the data of examples 8a and 8b show that different combinations of components may be used to effectively form the emulsions of the present invention. Due to the low interfacial tension between the fluorochemical and drug containing co-solvent phase the formation of relatively stable liquid-liquid dispersions (i.e. reverse emulsions) is possible with out the use of surfactants.

EXAMPLE 9

Preparation Of A Submicron Sized Ciprofloxacin Suspension in Fluorochemicals Three milliliters of the following submicron sized fluorochemical suspension was prepared:
Composition 1: 0.35, w/v, Cyprofloxaxin. HCl (Miles, Inc.) was dissolved in the presence of 100 mg $Na_2Co_3$ (NF Grade, Spectrum Chemical) into a solution composed of 1,4-dibromo-F-butane (50%,v/v; Exfluor, Austin, Tex.) and NF grade ethyl alcohol (50%,v/v; Spectrum Chemical Co). Fluorochemical Diluent: Perfluorooctylbromide (Atochem, France).

An aliquot of composition 1 (90 µL) was injected with a syringe into a sample of perfluorooctylbromide (PFOB; 3 mL) contained in a 12×100 mm test tube. The tube was capped and gently mixed by inverting the tube. An opalescent submicron sized drug in fluorocarbon suspension was obtained. The particle size distribution of the dispersions was measured using photon correlation spectroscopy (PCS) on a Nicomp 270 photon correlation spectrophotometer (Pacific Scientific). The resulting drug dispersion had an average particle diameter of 55±47 nm.

This example further shows the ability of the present invention form high bioavailability pharmaceutical microdispersions incorporating a wide variety of pharmaceutical agents.

EXAMPLE 10

In Vitro Efficacy Of A Submicron Sized Antibiotic (Ciprofloxacin) Suspension The ciprofloxacine suspension prepared in example 9 was evaluated with respect to its antibacterial activity using techniques standard in the art. To mimic bacterial infection in the lung, for each sample evaluated, an *E. coli* suspension culture was maintained in a well with a monolayer of normal human bronchial/tracheal epithelial cells. The experimental procedure is followed:

a). Prepare a monolayer of normal human lung epithelial cells.

b). Add 60 µL of *E. coli* culture into the well with lung epithelial cells on the 96-well plate.

c). Culture 1 hr at 37° C., then add 100 µL of either a Ciprofloxacin/PFOB suspension or a control solution into each well where a total of 1 mL culture media is present. Incubate at 37° C. overnight.

d). Aspirate the cultured mixture and diluted with LB media (1:2).

e). Take 20 µL of diluted mixture and plate on an LB plate for an initial titration of *E. coli*. The *E. coli* plates were incubated at 37° C. overnight.

f). Various dilutions were made according to the initial titer of each mixture so as to determine the accurate titer in each well. A duplicated set of tests was conducted for each treatment.

g). The titer of *E. coli* was calculated by multiplying the number of colonies grown on each plate by a dilution factor for each well tested.

h). The level of cell toxicity was evaluated by the cell shape, viability and density under the microscope.

The results are summarized in Table 8 directly below:

TABLE 8

| Antibacterial Efficacy and Relative Human Lung Epithelial Cell Toxicity for a Ciprofloxacin Suspension in Perfluorooctyl Bromide | | | |
|---|---|---|---|
| Well No. | Ciprofloxacin concentration (mg/mL)/Sample | Relative Cell Toxicity* | *E. coli* titer (colonies/ml) |
| 1 | 0.03/sol | 0–1 | 10 |
| 2 | 0.06/sol | 0–1 | 0 |
| 3 | 0.1/sol | 0–1 | 0 |
| 4 | 0.05/saline | 0–1 | 0 |
| 5 | 0.1/saline | 1 | 0 |
| 6 | 0/negative control (no *E. coli* added) | No epithelial cells added | 60 |
| 7 | 0.6/saline | 0–1 | 0 |
| 8 | 0/saline | 5 | $7.04 \times 10^7$ |
| 9 | 0/PFOB | 3–4 | $1.82 \times 10^7$ |
| 10 | 0/1,4-dibromo-F-butane | 3 | $9.7 \times 10^6$ |
| 11 | 0/(1%, v/v, 1,4-dibromo-F-butane in PFOB | 3–4 | $1.25 \times 10^7$ |
| 12 | 0/no solution added | 5 | $6.28 \times 10^7$ |

*Higher values indicate higher relative toxicity.

Those skilled in the art will appreciate that the data above indicates that:

1). All of the ciprofloxacin suspensions in PFOB demonstrated equivalent antibacterial capacity with their corresponding positive controls, i.e. antibiotics dissolved in saline or buffer.

2). A dose response of antibacterial ability was observed.

3). The negative controls, treatments by saline and vehicle alone or no treatment at all for the *E.coli* suspension cultures, exhibited no inhibition of bacterial growth.

4). The controls with the treatments by PFOB, 1,4-dibromo-F-butane, and 1,4-dibromo-F-butane in PFOB were shown to exhibit no enhancement of bacterial growth or a slight decrease of bacteria growth.

5). The formulation tested did not exert any significant toxicity on epithelial cells.

Accordingly, the data above shows that the preparation of substantially homogeneous microdispersions in accordance with the present invention does not adversely effect the efficacy of the incorporated pharmaceutical agent. Further, the example clearly demonstrates the safety and efficacy of the microdispersions themselves. Those skilled in the art will appreciate that such results strongly indicate that these pharmaceutical microdispersions will exert the same bactericidal actions in vivo.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the present invention.

What is claimed is:

1. A method for preparing a pharmaceutical microdispersion exhibiting enhanced bioavailability, said method comprising the steps of:

providing a thermodynamically stable pharmaceutical composition comprising at least one lipophilic pharmaceutical agent incorporated in a physiologically acceptable liquid carrier, said liquid carrier comprising one or more lipophilic fluorochemicals and at least one non-fluorinated co-solvent; and combining said stable pharmaceutical composition with an amount of at least one fluorochemical diluent less lipophilic than said one or more lipophilic fluorochemicals, said fluorochemical diluent present in an amount sufficient to initiate phase separation of said at least one lipophilic pharmaceutical agent from said pharmaceutical composition wherein a pharmaceutical microdispersion is formed.

2. The method of claim 1 wherein said pharmaceutical microdispersion is a suspension.

3. The method of claim 1 wherein said pharmaceutical microdispersion is a reverse emulsion.

4. The method of claim 1 wherein said one or more lipophilic fluorchemical is selected from the group consisting of halogenated fluorochemicals, fluorocarbon-hydrocarbon diblock or triblock compounds, halogenated ethers, polyethers, fluorocarbon-hydrocarbon esters, fluorocarbon-hydrocarbon thioesters, fluorocarbon-hydrocarbon amines and fluorocarbon-hydrocarbon amides.

5. The method of claim 1 wherein said one or more lipophilic fluorochemicals are selected from the group consisting of: $C_nF_{2n+1}X$, $XC_nF_{2n}X$, where n=3–8, X=Br, Cl or I; $C_nF_{2n+1}\text{—}_mH_{2m+1}$, $C_nF_{2n+1}CH=CHC_mH_{2m+1}$, where n=2–8 m=2–6; $C_pH_{2p+1}\text{—}_nF_{2n}\text{—}_mH_{2m+1}$, where p=2–6, m=2–6 and n=2–8; $XC_nF_{2n}OC_mF_{2m}X$, $XCF_2OC_nF_{2n}OCF_2X$, where n=1–4, m=1–4, X=Br, Cl or I; $C_nF_{2n}\text{—}O\text{—}C_mH_{2m+1}$, where n=2–8; m=2–6; $C_pH_{2p+1}\text{—}O\text{—}C_nF_{2n}\text{—}O\text{—}C_mH_{2m+1}$, where p=2–6, m=2–6 and n=2–8; 1-bromo-F-octane (n-$C_8F_{17}$Br); 1-bromo-F-heptane (n-$C_7F_{15}$Br); 1-bromo-F-hexane (n-$C_6F_{13}$Br) 1-bromo-F-Butane (n-$C_4F_9$Br); perfluorooctyl chloride (n-$C_7F_{15}$Cl); 1,6-dichloro-F-hexane (n-$ClC_6F_{12}$Cl); 1,4-dichloro-F-butane (n-$ClC_4F_8$Cl); 1,4-dibromo-F-butane and 1,6-dibromo-F-hexane.

6. The method of claim 1 wherein said at least one lipophilic pharmaceutical agent is selected from the group consisting of respiratory drugs, antibiotics, anti-inflammatories, antineoplastics, anesthetics, ophthalmic agents, chemotherapeutic agents, cardiovascular agents, imaging agents and combinations thereof.

7. The method of claim 1 wherein said at least one lipophilic pharmaceutical agent exhibits a log of the Octanol/water partition coefficient (Log Po/w) greater than about 0.5.

8. The method of claim 1 wherein said at least one fluorochemical diluent is selected from the group consisting of bis(F-alkyl) ethenes, cyclic fluorocarbons, perfluorinated amines, brominated perfluorocarbons, perfluorooctyl chloride, perfluorooctyl hydride, perfluoroalkylated ethers perfluoroalkylated polyethers, fluorocarbon-hydrocarbon compounds and combinations thereof.

9. The method of claim 1 wherein said at least one nonfluorinated co-solvent is selected from the group consisting of ethers, alcohols, alkyl sulfoxides, and combinations thereof.

10. The method of claim 1 further comprising the step of introducing a therapeutically beneficial amount of a physiologically acceptable gas into said pharmaceutical microdispersion.

11. The method of claim 1 further comprising the step of adding a fluorinated or nonfluorinated surfactant.

12. The method of claim 1 wherein the concentration of said at least one lipophilic pharmaceutical agent is less than approximately 10% w/v and the concentration of said lipophilic fluorochemical is less than approximately 50% v/v.

13. The method of claim 1 wherein said microdispersion has an average particle diameter less than approximately 3 μm.

14. The method of claim 13 wherein said microdispersion has an average particle diameter less than approximately 1 μm.

15. A pharmaceutical microdispersion exhibiting enhanced bioavailability prepared according to the method of claim 1.

16. A pharmaceutical microdispersion exhibiting enhanced bioavailability prepared according to the method of claim 2.

17. A pharmaceutical microdispersion exhibiting enhanced bioavailability prepared according to the method of claim 3.

18. A pharmaceutical microdispersion exhibiting enhanced bioavailability prepared according to the method of claim 14.

19. A high bioavailability pharmaceutical formulation comprising:

a substantially homogeneous microdispersion of a pharmaceutically effective amount of at least one lipophilic pharmaceutical agent in a liquid continuous phase, said liquid continuous phase comprising one or more physiologically acceptable lipophilic fluorochemicals, at least one nonfluorinated co-solvent and at least one fluorochemical diluent wherein the fluorochemical diluent is less lipophilic than the lipophilic fluorochemical, said substantially homogeneous microdispersion being formed upon combination of the fluorochemical diluent with the lipophilic fluorochemical.

20. The high bioavailability pharmaceutical formulation of claim 19 wherein said substantially homogeneous microdispersion is a suspension.

21. The high bioavailability pharmaceutical formulation of claim 19 wherein said substantially homogeneous microdispersion is a reverse emulsion.

22. The high bioavailability pharmaceutical formulation of claim 19 wherein said one or more physiologically acceptable lipophilic fluorchemical is selected from the group consisting of halogenated fluorochemicals, fluorocarbon-hydrocarbon diblock or triblock compounds, halogenated ethers, polyethers, fluorocarbon-hydrocarbon esters, fluorocarbon-hydrocarbon thioesters, fluorocarbon-hydrocarbon amines and fluorocarbon-hydrocarbon amides.

23. The high bioavailability pharmaceutical formulation of claim 19 wherein said at least one lipophilic pharmaceutical agent is selected from the group consisting of respiratory drugs, antibiotics, anti-inflammatories, antineoplastics, anesthetics, ophthalmic agents, cardiovascular agents, imaging agents and combinations thereof.

24. The high bioavailability pharmaceutical formulation of claim 19 wherein said at least one lipophilic pharmaceutical agent exhibits an Octanol/water partition log coefficient (Log Po/w) greater than about 0.5.

25. The high bioavailability pharmaceutical formulation of claim 19 wherein said at least one fluorochemical diluent is selected from the group consisting of bis(F-alkyl) ethenes, cyclic fluorocarbons, perfluorinated amines, brominated perfluorocarbons, perfluorooctyl chloride, perfluorooctyl hydride, perfluoroalkylated ethers perfluoroalkylated polyethers, fluorocarbon-hydrocarbon compounds and combinations thereof.

26. The high bioavailability pharmaceutical formulation of claim 19 wherein said at least one nonfluorinated co-solvent is selected from the group consisting of ethers, alcohols, alkyl sulfoxides, and combinations thereof.

27. The high bioavailability pharmaceutical formulation of claim 19 wherein the concentration of said at least one lipophilic pharmaceutical agent is less than approximately 10% w/v and the concentration of said one or more lipophilic fluorochemicals is less than approximately 50% v/v.

28. The high bioavailability pharmaceutical formulation of claim 19 wherein the microdispersion has an average particle diameter less than 1 µm.

29. The high bioavailability pharmaceutical formulation of claim 19 wherein a therapeutically beneficial amount of a physiologically acceptable gas is incorporated in said liquid continuous phase.

30. The high bioavailability pharmaceutical formulation of claim 19 further comprising a fluorinated or nonfluorinated surfactant.

31. A method for delivering one or more lipophilic pharmaceutical agents to a physiologic target site, said method comprising the steps of:

providing a high bioavailability pharmaceutical formulation comprising a substantially homogeneous microdispersion of at least one lipophilic pharmaceutical agent in a liquid continuous phase, said liquid continuous phase comprising one or more lipophilic fluorochemicals, at least one nonfluorinated co-solvent and at least one fluorochemical diluent wherein the fluorochemical diluent is less lipophilic than the lipophilic fluorochemical, said substantially homogeneous microdispersion being formed upon combination of the fluorochemical diluent with the lipophilic fluorochemical; and introducing a pharmaceutically effective amount of said high bioavailability pharmaceutical formulation to a physiologic target site.

32. The method of claim 31 wherein said pharmaceutical formulation is a suspension.

33. The method of claim 31 wherein said pharmaceutical formulation is a reverse emulsion.

34. The method of claim 31 wherein said one or more lipophilic fluorochemical is selected from the group consisting of halogenated fluorochemicals, fluorocarbon-hydrocarbon diblock or triblock compounds, halogenated ethers, polyethers, fluorocarbon-hydrocarbon esters, fluorocarbon-hydrocarbon thioesters, fluorocarbon-hydrocarbon amines and fluorocarbon-hydrocarbon amides.

35. The method of claim 31 wherein said at least one lipophilic pharmaceutical agent is selected from the group consisting of respiratory drugs, antibiotics, anti-inflammatories, antineoplastics, anesthetics, ophthalmic agents, cardiovascular agents, imaging agents and combinations thereof.

36. The method of claim 31 wherein said at least one lipophilic pharmaceutical agent exhibits a log of the Octanol/water partition coefficient (Log Po/w) greater than about 0.5.

37. The method of claim 31 wherein said at least one fluorochemical diluent is selected from the group consisting of bis(F-alkyl) ethenes, cyclic fluorocarbons, perfluorinated amines, brominated perfluorocarbons, perfluorooctyl chloride, perfluorooctyl hydride, perfluoroalkylated ethers perfluoroalkylated polyethers, fluorocarbon-hydrocarbon compounds and combinations thereof.

38. The method of claim 31 wherein said at least one nonfluorinated co-solvent is selected from the group consisting of ethers, alcohols, alkyl sulfoxides, and combinations thereof.

39. The method of claim 31 wherein the concentration of said at least one lipophilic pharmaceutical agent is less than approximately 10% w/v and the concentration of said one or more lipophilic fluorochemicals is less than approximately 50% v/v.

40. The method of claim 31 wherein said high bioavailability pharmaceutical formulation has an average particle size less than 1 µm.

41. The method of claim 31 further comprising the step of introducing a therapeutically beneficial amount of a physiologically acceptable gas into said high bioavailability pharmaceutical formulation.

42. The method of claim 31 wherein the introduction of said pharmaceutical formulation to the physiological target site is accomplished topically, subcutaneously, intramuscularly, intraperitoneally, nasally, pulmonarily, vaginally, rectally, aurally, orally or ocularly.

43. A method for preparing a pharmaceutical material, comprising the steps of:

providing a pharmaceutical composition comprising a lipophilic first fluorochemical liquid, a nonfluorinated co-solvent and a pharmaceutical agent in a single continuous phase; and adding to said pharmaceutical composition a sufficient amount of a second fluorochemical liquid less lipophilic than said first fluorochemical liquid that is miscible in said first fluorochemical liquid, thereby causing phase separation of said pharmaceutical agent to form a microdisperse discontinuous phase.

44. The method of claim 43, wherein said phase separation results in a reverse emulsion.

45. The method of claim 43, wherein said phase separation results in a suspension.

46. The method of claim 43, wherein said discontinuous phase comprises said nonfluorinated co-solvent and said pharmaceutical agent.

47. The method of claim 43, further comprising the step of storing said pharmaceutical composition for at least one week prior to said adding step.

48. A method for providing a kit for preparing a pharmaceutical preparation, comprising:

placing a first composition comprising a first lipophilic liquid fluorocarbon, a nonfluorinated co-solvent and a pharmaceutical agent in a single continuous phase in a first container; and adding a second liquid fluorocarbon miscible with said first lipophilic liquid fluorocarbon to a second container, wherein said second liquid fluorocarbon is less lipophilic than said first lipophilic liquid fluorocarbon, such that upon combination of said first composition and said second liquid fluorocarbon, a phase separation of said pharmaceutical agent occurs to form a microdisperse discontinuous phase comprising said pharmaceutical agent.

49. The method of claim 48, wherein said first composition comprises a nonfluorinated co-solvent selected from the group consisting of ethers, alcohols, alkyl sulfoxides, and combinations thereof.

50. The method of claim 48, wherein said discontinuous phase comprises said pharmaceutical agent and said co-solvent.

51. The method of claim 48, wherein said discontinuous phase comprises a suspension of said pharmaceutical agent.

52. The high bioavailability pharmaceutical formulation of claim 20 further comprising a fluorinated or nonfluorinated surfactant.

53. The high bioavailability pharmaceutical formulation of claim 20 wherein said suspension has an average particle diameter less than approximately 1 μm.

54. The method of claim 43 wherein said lipophilic first fluorochemical liquid is selected from the group consisting of: $C_nF_{2n+1}X$, $XC_nF_{2n}X$, where n=3–8, X=Br, Cl or I; $C_nF_{2n+1}$—$_mH_{2m+1}$, $C_nF_{2n+1}CH$=$CHC_mH_{2m+1}$, where n=2–8 m=2–6; $C_pH_{2p+1}$—$_nF_{2n}$—$_mH_{2m+1}$, where p =2–6, m=2–6 and n=2–8; $XC_nF_{2n}OC_mF_{2m}X$, $XCF_2OC_nF_{2n}OCF_2X$, where n=1–4, m=1–4, X=Br, Cl or I; $C_nF_{2n}$—O—$C_mH_{2m+1}$, where n=2–8; m=2–6; $C_pH_{2p+1}$—O—$C_nF_{2n}$—O—$C_mH_{2m+1}$, where p=2–6, m=2–6 and n=2–8; 1-bromo-F-octane (n-$C_8F_{17}$Br); 1-bromo-F-heptane (n-$C_7F_{15}$Br); 1-bromo-F-hexane (n-$C_6F_{13}$Br) 1-bromo-F-Butane (n-$C_4F_9$Br); perfluorooctyl chloride (n-$C_7F_{15}$Cl); 1, 6-dichloro-F-hexane (n-$ClC_6F_{12}$Cl); 1, 4-dichloro-F-butane (n-$ClC_4F_8$Cl); 1, 4 -dibromo-F-butane and 1,6-dibromo-F-hexane.

55. The method of claim 43 wherein said pharmaceutical agent is selected from the group consisting of respiratory drugs, antibiotics, anti-inflammatories, antineoplastics, anesthetics, ophthalmic agents, chemotherapeutic agents, cardiovascular agents, imaging agents and combinations thereof.

56. The method of claim 43 further comprising the step of introducing a therapeutically beneficial amount of a physiologically acceptable gas into said pharmaceutical material.

57. The method of claim 45 further comprising the step of adding a fluorinated or nonfluorinated surfactant.

58. The method of claim 45 wherein said suspension has an average particle diameter less than approximately 1 μm.

59. The method of claim 48 wherein said first lipophilic fluorochemical liquid is selected from the group consisting of: $C_nF_{2n+1}X$, $XC_nF_{2n}X$, where n=3–8, X=Br, Cl or I; $C_nF_{2n}+1$—$_mH_{2m+1}$, $C_nF_{2n+1}CH$=$CHC_mH_{2m+1}$, where n=2–8 m=2–6; $C_pH_{2p+1}$—$_nF_{2n}$—$_mH_{2m+1}$, where p =2–6, m=2–6 and n=2–8; $XC_nF_{2n}OC_mF_{2m}X$, $XCF_2OC_nF_{2n}OCF_2X$, where n=1–4, m=1–4, X=Br, Cl or I; $C_nF_{2n}$—O—$C_mH_{2m+1}$, where n=2–8; m=2–6; $C_pH_{2p+1}$—O—$C_nF_{2n}$—O—$C_mH_{2m+1}$, where p=2–6, m=2–6 and n=2–8; 1-bromo-F-octane (n-$C_8F_{17}$Br); 1-bromo-F-heptane (n-$C_7F_{15}$Br); 1-bromo-F-hexane (n-$C_6F_{13}$Br) 1-bromo-F-Butane (n-$C_4F_9$Br); perfluorooctyl chloride (n-$C_7F_{15}$Cl); 1, 6-dichloro-F-hexane (n-$ClC_6F_{12}$Cl); 1, 4-dichloro-F-butane (n-$ClC_4F_8$Cl); 1, 4-dibromo-F-butane and 1,6-dibromo-F-hexane.

60. The method of claim 48 wherein said second liquid fluorocarbon is selected from the group consisting of bis(F-alkyl) ethenes, cyclic fluorocarbons, perfluorinated amines, brominated perfluorocarbons, perfluorooctyl chloride, perfluorooctyl hydride, perfluoroalkylated ethers perfluoroalkylated polyethers, fluorocarbon-hydrocarbon compounds and combinations thereof.

61. The method of claim 48 wherein said pharmaceutical agent is selected from the group consisting of respiratory drugs, antibiotics, anti-inflammatories, antineoplastics, anesthetics, ophthalmic agents, chemotherapeutic agents, cardiovascular agents, imaging agents and combinations thereof.

62. The method of claim 51 further comprising the step of adding a fluorinated or nonfluorinated surfactant.

63. The method of claim 54 wherein said suspension has an average particle diameter less than approximately 1 μm.

* * * * *